(12) United States Patent
Quintero et al.

(10) Patent No.: US 11,883,264 B2
(45) Date of Patent: *Jan. 30, 2024

(54) SKIN CLOSURE SYSTEMS AND DEVICES OF IMPROVED FLEXIBILITY AND STRETCHABILITY FOR BENDABLE JOINTS

(71) Applicant: Ethicon, Inc., Somerville, NJ (US)

(72) Inventors: Julian Quintero, Flemington, NJ (US); Kevin S. Weadock, Hillsborough, NJ (US); Leo B. Kriksunov, Ithaca, NY (US); Robert J. Tannhauser, Bridgewater, NJ (US)

(73) Assignee: Ethicon, Inc., Raritan, NJ (US)

( * ) Notice: Subject to any disclaimer, the term of this patent is extended or adjusted under 35 U.S.C. 154(b) by 329 days.

This patent is subject to a terminal disclaimer.

(21) Appl. No.: 16/598,249

(22) Filed: Oct. 10, 2019

(65) Prior Publication Data

US 2020/0038253 A1 Feb. 6, 2020

Related U.S. Application Data

(63) Continuation of application No. 15/467,537, filed on Mar. 23, 2017, now Pat. No. 10,470,935.

(51) Int. Cl.
*A61F 13/02* (2006.01)
*A61L 15/58* (2006.01)
*A61F 13/00* (2006.01)

(52) U.S. Cl.
CPC ........ *A61F 13/0253* (2013.01); *A61F 13/025* (2013.01); *A61F 13/0243* (2013.01); *A61L 15/585* (2013.01); *A61F 2013/0071* (2013.01); *A61F 2013/00451* (2013.01); *A61F 2013/00459* (2013.01); *A61F 2013/00548* (2013.01);

(Continued)

(58) Field of Classification Search
CPC .......... A61B 17/085; A61B 2017/0065; A61F 13/0269; A61F 13/025; A61F 13/0253; A61F 13/0243; A61F 2013/00451
See application file for complete search history.

(56) References Cited

U.S. PATENT DOCUMENTS

| 167,162 A | 8/1875 | French |
| 1,656,199 A | 1/1928 | Ensley |

(Continued)

FOREIGN PATENT DOCUMENTS

| AU | 2005-215776 A | 9/2005 |
| CA | 2262408 A | 8/2000 |

(Continued)

OTHER PUBLICATIONS

U.S. Appl. No. 12/207,984, filed Sep. 10, 2008, US-2009-0076542-A1, U.S. Pat. No. 9,655,622, May 23, 2017, Grant, Jonn, et al.

(Continued)

*Primary Examiner* — Alexander J Orkin

(57) ABSTRACT

A system or device for skin closure comprises an elastic flat flexible tape elongated along a longitudinal axis and having a lower side and an opposing upper side, said tape having a pressure sensitive adhesive on at least a portion of the lower side, said tape having a plurality of openings arranged side-by-side with spaces between said openings oriented across the longitudinal axis.

15 Claims, 11 Drawing Sheets

(52) U.S. Cl.
CPC ............... *A61F 2013/00553* (2013.01); *A61F 2013/00659* (2013.01)

(56) References Cited

U.S. PATENT DOCUMENTS

| | | | |
|---|---|---|---|
| 2,399,545 A * | 4/1946 | Davis | A61F 13/0226 |
| | | | 604/389 |
| 2,508,855 A | 5/1950 | Brown | |
| 2,721,858 A | 10/1955 | Joyner et al. | |
| 2,722,220 A | 11/1955 | Mestrand | |
| 2,807,262 A | 9/1957 | Lew | |
| 2,905,174 A | 5/1959 | Smith | |
| 3,085,572 A * | 4/1963 | Blackford | A61F 13/0206 |
| | | | 442/151 |
| 3,254,111 A | 5/1966 | Hawkins et al. | |
| 3,402,716 A | 9/1968 | Baxter | |
| 3,520,300 A | 7/1970 | Flower, Jr. | |
| 3,731,683 A | 5/1973 | Zaffaroni | |
| 3,888,247 A | 6/1975 | Stenvall | |
| 3,940,362 A | 2/1976 | Overhults | |
| 3,983,878 A | 10/1976 | Kawchitch | |
| 3,995,641 A | 12/1976 | Kronenthal et al. | |
| 4,068,664 A | 1/1978 | Sharp et al. | |
| 4,080,348 A | 3/1978 | Korpman | |
| 4,126,130 A | 11/1978 | Cowden et al. | |
| 4,140,115 A | 2/1979 | Schonfeld | |
| 4,263,906 A | 4/1981 | Finley | |
| 4,313,865 A | 2/1982 | Teramoto et al. | |
| 4,340,043 A | 7/1982 | Seymour | |
| 4,364,876 A | 12/1982 | Kimura et al. | |
| 4,390,519 A | 6/1983 | Sawyer | |
| 4,460,369 A | 7/1984 | Seymour | |
| 4,560,723 A | 12/1985 | Millet et al. | |
| 4,584,355 A | 4/1986 | Blizzard et al. | |
| 4,585,836 A | 4/1986 | Homan et al. | |
| 4,591,622 A | 5/1986 | Blizzard et al. | |
| 4,612,230 A | 9/1986 | Liland et al. | |
| 4,614,183 A | 9/1986 | McCracken et al. | |
| 4,630,603 A | 12/1986 | Greenway | |
| 4,655,767 A | 4/1987 | Woodard et al. | |
| 4,671,266 A | 6/1987 | Legnyel et al. | |
| 4,720,513 A | 1/1988 | Kameyama et al. | |
| 4,728,380 A * | 3/1988 | Jones | A61F 13/025 |
| | | | 156/230 |
| 4,733,659 A | 3/1988 | Edenbaum et al. | |
| 4,767,401 A | 8/1988 | Seiderman | |
| 4,793,887 A | 12/1988 | Card et al. | |
| 4,793,888 A | 12/1988 | Card et al. | |
| 4,795,435 A | 1/1989 | Steer et al. | |
| 4,852,571 A | 8/1989 | Gadsby et al. | |
| 4,867,747 A | 9/1989 | Yarger | |
| 4,872,450 A | 10/1989 | Austad | |
| 4,950,282 A | 8/1990 | Beisang et al. | |
| 4,966,605 A | 10/1990 | Thieler | |
| 4,999,235 A | 3/1991 | Lunn et al. | |
| 5,035,687 A | 7/1991 | Sandbank | |
| 5,059,424 A | 10/1991 | Cartmell et al. | |
| 5,086,763 A | 2/1992 | Hathman | |
| 5,088,483 A | 2/1992 | Heinecke | |
| 5,106,362 A | 4/1992 | Gilman | |
| 5,125,907 A | 6/1992 | Philpott | |
| 5,164,444 A | 11/1992 | Bernard | |
| 5,173,302 A | 12/1992 | Holmblad et al. | |
| 5,232,958 A | 8/1993 | Mallya et al. | |
| 5,254,132 A | 10/1993 | Barley et al. | |
| 5,259,835 A | 11/1993 | Clark et al. | |
| 5,266,371 A | 11/1993 | Sugii et al. | |
| D347,059 S | 5/1994 | Mota | |
| 5,308,313 A | 5/1994 | Karami et al. | |
| 5,328,687 A | 7/1994 | Leung et al. | |
| 5,336,209 A | 8/1994 | Porzilli | |
| 5,415,626 A | 5/1995 | Goodman et al. | |
| 5,429,592 A | 7/1995 | Jensen | |
| 5,445,597 A | 8/1995 | Clark et al. | |
| 5,449,340 A | 9/1995 | Tollini | |
| D363,126 S | 10/1995 | Dusek | |
| 5,456,660 A | 10/1995 | Reich et al. | |
| 5,476,440 A | 12/1995 | Edenbaum | |
| 5,486,547 A | 1/1996 | Matsuda et al. | |
| D370,258 S | 5/1996 | Newman | |
| D373,750 S | 9/1996 | Gunderson | |
| 5,571,079 A | 11/1996 | Bello et al. | |
| 5,575,997 A | 11/1996 | Leung et al. | |
| 5,582,834 A | 12/1996 | Leung et al. | |
| 5,599,858 A | 2/1997 | Buchanan et al. | |
| 5,620,702 A | 4/1997 | Podell et al. | |
| 5,623,011 A | 4/1997 | Bernard | |
| 5,624,669 A | 4/1997 | Leung et al. | |
| D382,343 S | 8/1997 | Wandell et al. | |
| 5,653,769 A | 8/1997 | Barley, Jr. et al. | |
| D383,211 S | 9/1997 | Dunshee et al. | |
| 5,662,599 A | 9/1997 | Reich et al. | |
| D387,169 S | 12/1997 | Dunshee et al. | |
| D389,244 S | 1/1998 | Dunshee et al. | |
| 5,705,551 A | 1/1998 | Sasaki et al. | |
| D391,639 S | 3/1998 | Dunshee et al. | |
| 5,749,895 A | 5/1998 | Sawyer et al. | |
| 5,762,955 A | 6/1998 | Smith | |
| 5,780,048 A | 7/1998 | Lee | |
| 5,782,788 A | 7/1998 | Widemire | |
| 5,823,983 A | 10/1998 | Rosofsky et al. | |
| 5,823,986 A | 10/1998 | Peterson | |
| D402,371 S | 12/1998 | Haynes et al. | |
| D403,425 S | 12/1998 | Hinds et al. | |
| D404,139 S | 1/1999 | Young | |
| 5,861,348 A | 1/1999 | Kase | |
| 5,876,745 A | 3/1999 | Muraoka et al. | |
| 5,902,443 A | 5/1999 | Kanakubo et al. | |
| 5,928,611 A | 7/1999 | Leung | |
| 5,931,800 A | 8/1999 | Rasmussen et al. | |
| 5,947,917 A | 9/1999 | Carté et al. | |
| 5,951,505 A | 9/1999 | Gilman et al. | |
| 5,998,694 A | 12/1999 | Jensen et al. | |
| D424,699 S | 5/2000 | Allen | |
| 6,093,465 A | 7/2000 | Gilchrist et al. | |
| 6,125,265 A | 9/2000 | Yamamoto et al. | |
| 6,140,548 A | 10/2000 | Hansen et al. | |
| 6,143,352 A | 11/2000 | Clark et al. | |
| 6,155,265 A | 12/2000 | Hammerslag | |
| 6,183,593 B1 | 2/2001 | Narang et al. | |
| D439,973 S | 4/2001 | Choksi | |
| 6,217,603 B1 | 4/2001 | Clark et al. | |
| 6,238,692 B1 | 5/2001 | Smith | |
| 6,245,960 B1 | 6/2001 | Eaton | |
| 6,284,941 B1 | 9/2001 | Cox et al. | |
| 6,310,166 B1 | 10/2001 | Hickey et al. | |
| 6,329,564 B1 | 12/2001 | Lebner | |
| 6,352,704 B1 | 3/2002 | Nicholson et al. | |
| D458,687 S | 6/2002 | Dale et al. | |
| 6,410,818 B1 | 6/2002 | Oyaski | |
| 6,439,789 B1 | 8/2002 | Balance et al. | |
| D463,564 S | 9/2002 | Siegwart et al. | |
| 6,455,064 B1 | 9/2002 | Narang et al. | |
| 6,479,725 B1 | 11/2002 | Brothers | |
| 6,482,431 B2 | 11/2002 | Smith | |
| 6,512,023 B1 | 1/2003 | Malofsky et al. | |
| D471,984 S | 3/2003 | Dunshee et al. | |
| D472,319 S | 3/2003 | Oltmann | |
| 6,559,350 B1 | 5/2003 | Tetreault et al. | |
| 6,579,469 B1 | 6/2003 | Nicholson et al. | |
| 6,582,713 B2 | 6/2003 | Newell et al. | |
| D477,076 S | 7/2003 | Wall | |
| 6,589,269 B2 | 7/2003 | Zhu et al. | |
| 6,595,940 B1 | 7/2003 | D'Alessio et al. | |
| 6,596,917 B2 | 7/2003 | Oyaski | |
| 6,599,318 B1 | 7/2003 | Gabbay | |
| 6,620,846 B1 | 9/2003 | Jonn et al. | |
| D480,879 S | 10/2003 | Boehm et al. | |
| 6,632,450 B1 | 10/2003 | Gregory | |
| 6,635,272 B2 | 10/2003 | Leaderman | |
| 6,652,559 B1 | 11/2003 | Tetreault et al. | |
| 6,667,051 B1 | 12/2003 | Gregory | |
| 6,712,839 B1 | 3/2004 | Lönne | |
| 6,787,682 B2 | 9/2004 | Gilman | |

(56) References Cited

U.S. PATENT DOCUMENTS

| | | | |
|---|---|---|---|
| 6,837,027 B2 | 1/2005 | Hickey | |
| 6,841,716 B1 | 1/2005 | Tsutsumi | |
| 6,942,683 B2 | 9/2005 | Dunshee | |
| D515,701 S | 2/2006 | Horhota et al. | |
| D516,728 S | 3/2006 | Wall | |
| D520,639 S | 5/2006 | Dodd et al. | |
| 7,041,124 B2* | 5/2006 | Purcell | A61F 7/034 128/898 |
| 7,044,982 B2 | 5/2006 | Milbocker | |
| 7,066,934 B2 | 6/2006 | Kirsch | |
| 7,122,712 B2 | 10/2006 | Lutri et al. | |
| 7,144,390 B1 | 12/2006 | Hannigan et al. | |
| 7,164,054 B2 | 1/2007 | Mori et al. | |
| D548,348 S | 8/2007 | Nash | |
| 7,252,837 B2 | 8/2007 | Guo et al. | |
| D562,461 S | 2/2008 | Nash et al. | |
| 7,371,400 B2 | 5/2008 | Borenstein et al. | |
| D574,962 S | 8/2008 | Atkins et al. | |
| D580,553 S | 11/2008 | Nash | |
| D581,467 S | 11/2008 | Winningham et al. | |
| 7,457,667 B2 | 11/2008 | Skiba | |
| D582,561 S | 12/2008 | Sachi | |
| D584,415 S | 1/2009 | Sachi | |
| 7,576,257 B2 | 8/2009 | LaGreca, Sr. | |
| D611,156 S | 3/2010 | Dunshee | |
| 7,713,463 B1 | 5/2010 | Reah et al. | |
| D618,810 S | 6/2010 | Tanigawa et al. | |
| D621,052 S | 8/2010 | Kase | |
| D621,053 S | 8/2010 | Kase | |
| D624,190 S | 9/2010 | Neri | |
| D632,398 S | 2/2011 | Bray et al. | |
| D636,881 S | 4/2011 | Clemens et al. | |
| 7,943,811 B2 | 5/2011 | Da Silva Macedo, Jr. | |
| 7,981,136 B2 | 7/2011 | Weiser | |
| 7,982,087 B2 | 7/2011 | Greener et al. | |
| D646,789 S | 10/2011 | Barth | |
| 8,343,606 B2 | 1/2013 | Marchitto et al. | |
| 8,353,966 B2 | 1/2013 | Day et al. | |
| D676,490 S | 2/2013 | Bratter et al. | |
| 8,372,051 B2 | 2/2013 | Scholz et al. | |
| D679,098 S | 4/2013 | Ogawa | |
| D679,402 S | 4/2013 | Conrad-Vlasak et al. | |
| D679,403 S | 4/2013 | Heinecke et al. | |
| D679,405 S | 4/2013 | Arbesman | |
| D679,819 S | 4/2013 | Peron | |
| D679,820 S | 4/2013 | Peron | |
| D685,484 S | 7/2013 | Brambilla | |
| 8,528,730 B2 | 9/2013 | Grossman | |
| D691,730 S | 10/2013 | Smith et al. | |
| D692,566 S | 10/2013 | Adoni | |
| D693,010 S | 11/2013 | Mosa et al. | |
| D694,892 S | 12/2013 | Chan et al. | |
| 8,603,053 B2 | 12/2013 | Riesinger | |
| D697,216 S | 1/2014 | Chan et al. | |
| 8,642,831 B2 | 2/2014 | Larsen et al. | |
| 8,663,171 B2 | 3/2014 | Tambourgi et al. | |
| D705,429 S | 5/2014 | Cheney et al. | |
| D707,829 S | 6/2014 | Chan et al. | |
| D708,751 S | 7/2014 | Chan et al. | |
| 8,777,986 B2 | 7/2014 | Straehnz et al. | |
| D712,045 S | 8/2014 | Thornton | |
| D713,534 S | 9/2014 | Manley, Jr. | |
| D713,967 S | 9/2014 | Adoni | |
| D714,575 S | 10/2014 | Mah | |
| 8,884,094 B2 | 11/2014 | Lockwood et al. | |
| D718,812 S | 12/2014 | Sukhbaatar | |
| 9,000,251 B2 | 4/2015 | Murphy et al. | |
| RE45,510 E | 5/2015 | Hisamitsu | |
| D728,803 S | 5/2015 | Sinda et al. | |
| D745,688 S | 12/2015 | Chan et al. | |
| D745,689 S | 12/2015 | Chan et al. | |
| D746,479 S | 12/2015 | Arefieg | |
| RE45,864 E | 1/2016 | Peron | |
| D746,996 S | 1/2016 | Karlsson et al. | |
| D750,789 S | 3/2016 | Mackay et al. | |
| D757,950 S | 5/2016 | Karlsson et al. | |
| 9,339,417 B2 | 5/2016 | Ogawa | |
| 9,381,284 B2 | 7/2016 | Cornet et al. | |
| 9,440,010 B2 | 9/2016 | Locke | |
| 9,492,171 B2 | 11/2016 | Patenaude | |
| 9,623,142 B2 | 4/2017 | Jonn et al. | |
| D786,350 S | 5/2017 | Nakai et al. | |
| D786,351 S | 5/2017 | Nakai et al. | |
| D786,352 S | 5/2017 | Nakai et al. | |
| D786,353 S | 5/2017 | Nakai et al. | |
| D786,972 S | 5/2017 | Nakai et al. | |
| 9,655,622 B2 | 5/2017 | Jonn et al. | |
| D790,071 S | 6/2017 | Ahsani | |
| D824,525 S | 7/2018 | Lacy et al. | |
| D833,526 S | 11/2018 | Nakai et al. | |
| 10,434,211 B2 | 10/2019 | Jonn et al. | |
| 10,470,935 B2* | 11/2019 | Quintero | A61F 13/0253 |
| 2001/0002432 A1 | 5/2001 | Bugge | |
| 2001/0028943 A1 | 10/2001 | Mashiko et al. | |
| 2001/0037077 A1 | 11/2001 | Wiemken | |
| 2001/0051178 A1* | 12/2001 | Blatchford | A61F 13/025 424/443 |
| 2002/0018689 A1 | 2/2002 | Badejo et al. | |
| 2002/0019652 A1 | 2/2002 | DaSilva et al. | |
| 2002/0037310 A1 | 3/2002 | Jonn et al. | |
| 2002/0039867 A1 | 4/2002 | Curro et al. | |
| 2002/0049503 A1 | 4/2002 | Milbocker | |
| 2002/0185396 A1 | 12/2002 | Mainwaring et al. | |
| 2002/0192107 A1 | 12/2002 | Hickey | |
| 2002/0193721 A1 | 12/2002 | Vandruff | |
| 2003/0031499 A1 | 2/2003 | Heard et al. | |
| 2003/0050590 A1 | 3/2003 | Kirsch | |
| 2003/0093024 A1 | 5/2003 | Falleiros et al. | |
| 2003/0100955 A1 | 5/2003 | Greenawalt et al. | |
| 2003/0109819 A1 | 6/2003 | Tsuruda et al. | |
| 2003/0125654 A1 | 7/2003 | Malik | |
| 2003/0175824 A1 | 9/2003 | Pishko et al. | |
| 2003/0220596 A1 | 11/2003 | Dunshee | |
| 2003/0225355 A1 | 12/2003 | Butler | |
| 2004/0001879 A1 | 1/2004 | Guo et al. | |
| 2004/0060867 A1 | 4/2004 | Kriksunov et al. | |
| 2004/0106888 A1 | 6/2004 | Lutri et al. | |
| 2004/0120849 A1 | 6/2004 | Stewart et al. | |
| 2004/0142041 A1 | 7/2004 | MacDonald et al. | |
| 2004/0162512 A1 | 8/2004 | Liedtke et al. | |
| 2004/0220505 A1 | 11/2004 | Worthley | |
| 2005/0015036 A1 | 1/2005 | Lutri et al. | |
| 2005/0043820 A1 | 2/2005 | Browning | |
| 2005/0085757 A1 | 4/2005 | Santanello | |
| 2005/0147457 A1 | 7/2005 | Badejo et al. | |
| 2005/0153090 A1 | 7/2005 | Marchitto et al. | |
| 2005/0154340 A1 | 7/2005 | Schlussel | |
| 2005/0182443 A1 | 8/2005 | Jonn et al. | |
| 2005/0208100 A1 | 9/2005 | Weber et al. | |
| 2005/0288706 A1 | 12/2005 | Widomski et al. | |
| 2006/0009099 A1 | 1/2006 | Jonn et al. | |
| 2006/0058721 A1 | 3/2006 | Lebner et al. | |
| 2006/0141012 A1 | 6/2006 | Gingras | |
| 2006/0173394 A1 | 8/2006 | Stroock et al. | |
| 2006/0265005 A1 | 11/2006 | Beese | |
| 2007/0106195 A1 | 5/2007 | Marcoux et al. | |
| 2007/0218101 A1 | 9/2007 | Johnson et al. | |
| 2007/0272211 A1 | 11/2007 | Kassner | |
| 2007/0282238 A1 | 12/2007 | Madsen et al. | |
| 2007/0299542 A1 | 12/2007 | Mathisen et al. | |
| 2008/0051687 A1 | 2/2008 | Rogers | |
| 2008/0154168 A1 | 2/2008 | Lutri | |
| 2008/0086113 A1 | 4/2008 | Tenney et al. | |
| 2008/0109034 A1 | 5/2008 | Mather et al. | |
| 2008/0110961 A1 | 5/2008 | Voegele et al. | |
| 2008/0167633 A1 | 7/2008 | Vannucci | |
| 2008/0228219 A1 | 9/2008 | Weiser | |
| 2008/0228220 A1 | 9/2008 | Weiser | |
| 2008/0280037 A1 | 11/2008 | Sheridan et al. | |
| 2008/0302487 A1 | 12/2008 | Goodman et al. | |
| 2009/0074842 A1 | 3/2009 | Hsu | |
| 2010/0106120 A1 | 4/2010 | Holm | |
| 2010/0198161 A1 | 8/2010 | Propp | |
| 2010/0262091 A1 | 10/2010 | Larsson | |

(56) References Cited

U.S. PATENT DOCUMENTS

| | | |
|---|---|---|
| 2010/0298791 A1 | 11/2010 | Jones et al. |
| 2011/0047766 A1 | 3/2011 | McAulay et al. |
| 2011/0071415 A1 | 3/2011 | Karwoski et al. |
| 2011/0092874 A1 | 4/2011 | Baschnagel |
| 2011/0130699 A1 | 6/2011 | Madsen et al. |
| 2011/0208102 A1 | 8/2011 | Chawki |
| 2011/0253303 A1 | 10/2011 | Miyachi et al. |
| 2012/0052230 A1 | 3/2012 | Olsson et al. |
| 2012/0220912 A1 | 8/2012 | Shang |
| 2012/0238933 A1 | 9/2012 | Murphy et al. |
| 2012/0277645 A1 | 11/2012 | Kikuta et al. |
| 2013/0012988 A1 | 1/2013 | Blume et al. |
| 2013/0041337 A1 | 2/2013 | Aali et al. |
| 2013/0066365 A1 | 3/2013 | Belson et al. |
| 2013/0084323 A1 | 4/2013 | Riebman et al. |
| 2013/0138068 A1 | 5/2013 | Hu et al. |
| 2013/0143326 A1 | 6/2013 | Tai et al. |
| 2013/0144399 A1 | 6/2013 | Tai et al. |
| 2013/0204077 A1 | 8/2013 | Nagale et al. |
| 2013/0218125 A1 | 8/2013 | Stopek et al. |
| 2013/0245784 A1 | 9/2013 | Tan et al. |
| 2013/0274717 A1 | 10/2013 | Dunn |
| 2013/0282049 A1 | 10/2013 | Peterson et al. |
| 2013/0317405 A1 | 11/2013 | Ha et al. |
| 2014/0024989 A1 | 1/2014 | Ueda |
| 2014/0107561 A1 | 4/2014 | Dorian et al. |
| 2014/0121649 A1 | 5/2014 | Calco |
| 2014/0155916 A1 | 6/2014 | Hodgkinson et al. |
| 2014/0171888 A1 | 6/2014 | Croizat et al. |
| 2014/0257348 A1 | 9/2014 | Priewe et al. |
| 2014/0257517 A1 | 9/2014 | Deichmann et al. |
| 2015/0057491 A1 | 2/2015 | Goddard et al. |
| 2015/0209186 A1 | 7/2015 | Abbott et al. |
| 2015/0257938 A1 | 9/2015 | Pensier |
| 2015/0297413 A1 | 10/2015 | Blanco |
| 2015/0314114 A1 | 11/2015 | La Rosa |
| 2015/0351767 A1 | 12/2015 | Zoll et al. |
| 2016/0030248 A1 | 2/2016 | Potters |
| 2016/0089145 A1 | 3/2016 | Quintero et al. |
| 2016/0199230 A1* | 7/2016 | Doshi ............... A61F 13/0246 156/219 |
| 2016/0296673 A1 | 10/2016 | Sambusseti |
| 2017/0035422 A1* | 2/2017 | Belson ............... A61B 17/085 |
| 2017/0056568 A1 | 3/2017 | Shelton, IV et al. |
| 2017/0056569 A1 | 3/2017 | Vendely et al. |
| 2017/0189159 A1 | 7/2017 | Bartee et al. |
| 2017/0273837 A1 | 9/2017 | Brueckner |
| 2017/0367806 A1 | 12/2017 | Gingras et al. |
| 2018/0085103 A1 | 3/2018 | Quintero et al. |
| 2018/0085259 A1 | 3/2018 | Quintero |
| 2018/0085260 A1 | 3/2018 | Quintero |
| 2019/0381207 A1 | 12/2019 | Jonn et al. |

FOREIGN PATENT DOCUMENTS

| | | |
|---|---|---|
| CN | 1697639 A | 11/2005 |
| CN | 201441532 U | 4/2010 |
| CN | 101965169 A | 2/2011 |
| CN | 102755216 A | 10/2012 |
| CN | 102781433 A | 11/2012 |
| CN | 203234898 A | 10/2013 |
| CN | 204766892 U | 11/2015 |
| EP | 0532275 A | 3/1993 |
| EP | 0730874 A | 9/1996 |
| EP | 0746293 A1 | 12/1996 |
| EP | 1161212 A | 8/2000 |
| EP | 2359782 A | 8/2011 |
| EP | 2377498 A | 10/2011 |
| EP | 2731563 A | 5/2014 |
| EP | 2531155 A | 10/2014 |
| EP | 2805698 A | 11/2014 |
| EP | 3574875 A1 | 12/2019 |
| GB | 2078763 A | 1/1982 |
| JP | 59-500046 A | 1/1984 |
| JP | 61-203020 A | 12/1986 |
| JP | 62-87624 A | 6/1987 |
| JP | 01-265967 A | 10/1988 |
| JP | 2-140948 A | 11/1990 |
| JP | 3-56429 U | 5/1991 |
| JP | 06-509966 A | 11/1994 |
| JP | 7-016258 A | 1/1995 |
| JP | 2001-265967 A | 9/2001 |
| JP | 1130927 S | 11/2001 |
| JP | 2002-512980 A | 5/2002 |
| JP | 2002-521139 A | 7/2002 |
| JP | 2002-537068 A | 11/2002 |
| JP | 2003-052741 A | 2/2003 |
| JP | 2003-153949 A | 5/2003 |
| JP | 58-124123 U | 1/2004 |
| JP | 2004-24905 A | 1/2004 |
| JP | 2006-061263 A | 3/2006 |
| JP | 2006-509966 A | 3/2006 |
| JP | 2007-522882 A | 8/2007 |
| JP | 3147394 U | 12/2008 |
| JP | 2009-022730 A | 2/2009 |
| JP | 1359502 S | 5/2009 |
| JP | 2011-004850 A | 1/2011 |
| JP | 1571238 S | 3/2017 |
| JP | 1629290 | 4/2019 |
| MX | 241113 A | 10/2006 |
| WO | WO 1983/002586 A | 8/1983 |
| WO | WO 1993/004650 A | 3/1993 |
| WO | WO 1995/004511 A | 2/1995 |
| WO | WO 1996/040797 A | 12/1996 |
| WO | WO 1998/026719 A | 6/1998 |
| WO | WO 2000/006213 A | 2/2000 |
| WO | WO 2000/049983 A | 8/2000 |
| WO | WO 2003/008002 A | 1/2003 |
| WO | WO 2004/049987 A | 6/2004 |
| WO | WO 2005/007020 A | 1/2005 |
| WO | WO 2005/051259 A | 6/2005 |
| WO | WO 2005/079674 A | 9/2005 |
| WO | WO 2006/017109 A | 2/2006 |
| WO | WO 2008/082444 A | 7/2008 |
| WO | WO 2009/067062 A | 5/2009 |
| WO | WO 2010/134873 A | 11/2010 |
| WO | 2011152368 A1 | 12/2011 |
| WO | WO 2013/009725 A | 1/2013 |
| WO | WO 2014/083570 A | 6/2014 |
| WO | WO 2014/195710 A | 12/2014 |
| WO | WO 2015/135351 A | 9/2015 |

OTHER PUBLICATIONS

U.S. Appl. No. 15/490,176, filed Apr. 18, 2017, US-2017-0216482, U.S. Pat. No. 10,434,211, Oct. 8, 2019, Grant, Jonn, et al.

U.S. Appl. No. 15/964,538, filed Apr. 27, 2018, US-2018-0243467, U.S. Pat. No. 10,398,802, Sep. 3, 2019, Grant, Jonn, et al.

U.S. Appl. No. 16/556,443, filed Aug. 30, 2019, US-2019-0381207, Publication, Jonn, et al.

U.S. Appl. No. 10/779,721, filed Feb. 18, 2004, US-2005-0182443-A1, Abandoned.

U.S. Appl. No. 16/556,471, filed Aug. 30, 2019, US-2019-0381206, Publication, Jonn, et al.

U.S. Appl. No. 12/163,021, filed Jun. 27, 2008, US-2008-0255610-A1, U.S. Pat. No. 9,623,142, Apr. 18, 2017, Grant, Jonn, et al.

U.S. Appl. No. 15/452,126, filed Mar. 7, 2017, US-2017-0173208, U.S. Pat. No. 10,398,800, Sep. 3, 2019, Grant, Jonn, et al.

U.S. Appl. No. 10/887,884, filed Jul. 12, 2004, US-2006-0009099-AI, Abandoned

U.S. Appl. No. 14/864,033, filed Sep. 24, 2015, US2016-0089145, Publication, Quintero, et al.

U.S. Appl. No. 16/387,634, filed Apr. 18, 2019, US-2019-0240074, Publication, Quintero, et al.

U.S. Appl. No. 29/635,782, filed Feb. 2, 2018, Filing, Quintero, et al.

U.S. Appl. No. 29/503,320, filed Sep. 25, 2014, U.S. Pat. No. D824,525, Jul. 31, 2018, Grant, Quintero, et al.

U.S. Appl. No. 29/648,487, filed May 22, 2018, U.S. Pat. No. D854,171, Jul. 16, 2019, Grant, Quintero, et al.

(56) References Cited

OTHER PUBLICATIONS

U.S. Appl. No. 29/690,950, filed May 13, 2019, Filing, Quintero, et al.
U.S. Appl. No. 15/675,159, filed Aug. 11, 2017, US-2018-0085260, U.S. Pat. No. 10,687,986, Jun. 23, 2020, Grant, Quintero, et al.
U.S. Appl. No. 16/907,930, filed Jun. 22, 2020, US-2020-0315858, Publication, Quintero, et al.
U.S. Appl. No. 29/613,662, filed Aug. 11, 2017, U.S. Pat. No. D848,624, May 14, 2019, Grant, Quintero, et al.
U.S. Appl. No. 29/683,074, filed Mar. 11, 2019, U.S. Pat. No. D907,217, Jan. 5, 2021, Grant, Quintero, et al.
U.S. Appl. No. 29/761,282, filed Dec. 8, 2020, Filing, Quintero, et al.
U.S. Appl. No. 15/280,303, filed Sep. 29, 2016, US-2018-0085259, U.S. Pat. No. 10,470,934, Nov. 12, 2019, Grant, Quintero, et al.
U.S. Appl. No. 16/598,249, filed Oct. 10, 2019, US-2020-0038253, Publication, Quintero, et al.
U.S. Appl. No. 15/467,537, filed Mar. 23, 2017, US-2018-0271712, U.S. Pat. No. 10,470,935, Nov. 12, 2019, Grant, Quintero, et al.
U.S. Appl. No. 17/143,883, filed Jan. 7, 2021, Filing, Quintero, et al.
U.S. Appl. No. 15/496,389, filed Apr. 25, 2017, US-2018-0303967, Publication, Quintero, et al.
U.S. Appl. No. 16/050,205, filed Jul. 31, 2018, US-2020-0038006, Publication, Quintero, et al.
JP 7040744, 1995, English claims.
JP 3059327, 1991, English claims.
Japanese Office Action dated Feb. 19, 2019 for Design Appln. No. 2018-017274.
Japanese Office Action dated Feb. 26, 2019 for Patent Appln. No. 515463.
3M™ Steri-Strip Adhesive Closures Product Catalog Brochure, (2011) 4 pages.
3M™ Steri-Strip Adhesive Closures Product Catalog Brochure, (2011) 8 pages.
3M™ Steri-Strip Adhesive Closures Product Catalog Brochure, (2012) 12 pages.
Allen, L.V. Jr et al Ansel's Pharmaceutical Dosage Forms and Drug Delivery Systems, 8th edition 2005 Lippincott Williams & Wilkins, Chapter 4, Dosage Form Design: Pharmaceutical and Formulation Considerations p. 131.
Ashley et al.: Further studies involving wound closure with a rapidly polymerizing adhesive; *Plastic and Reconstructive Surgery*; Apr. 1963; vol. 31; pp. 333-343.
Ashley et al.: Nonsutured closure of skin lacerations and nonsutured grafting of skin with a rapidly polymerizing adhesive; *Qtrly Bull. Northwestern University (Evanston, Ill.)* Medical School; 1962; vol. 36; pp. 189-194.
Brombeg et al.: Nonsuture fixation of split-thickness skin grafts; *Surgery*, Jun. 1964; vol. 55; pp. 846-853.
Cramer: Rapid Skin Grafting in Small Animals; *Plastic and Reconstructive Surgery and the Transplantation Bull*; Oct. 1962, vol. 30; pp. 149-150.
Cramer et al.: Autograft rejection induced by homografting. A phenomenon intermediate between homograft rejection and autoimmunity; *Plastic and Reconstructive Surgery*; Jun. 1965; vol. 35; pp. 572-587.
Demaria, E. 'New skin closure system facilitates wound healing after cardiovascular implantable electronic device surgery' World Journal of Clinical Cases (2015) 3(8) pp. 675-677.
Dermabond Prineo Skin Closure Systems (22 cm) Brochure (2014), 7 pages.
Dermabond Prineo Skin Closure Systems (22 cm) Brochure (2015), 2 pages.
Healthcare Packaging. Advanced Wound Care Products and packaging Needs. Jun. 5, 2017 (earliest online date), [site visited May 8, 2018]. Available from the Internet, URL:https://www.healthcarepackaging.com/article/applications/healthcare/advanced-wound-care-products-and-packaging-needs> (Year: 2017).

Inou: Studies on the Surgical Use of Plastic Adhesive; *Am. Journal of Proctology*; 1962; vol. 13; pp. 219-226.
Jesse et al.: Fixation of split-thickness skin grafts with adhesive; *Plastic and Reconstructive Surgery*; Mar. 1964; vol. 33; pp. 272-277.
Kaplan: A technique of nonsuture wound closure with a plastic tissue adhesive; *Plastic and Reconstructive Surgery*; Feb. 1966; vol. 37(2); pp. 139-142.
Keddie et al.: Intrafollicular tinea versicolor demonstrated on monomer plastic strips; *Journal of Investigative Dermatology*; Sep. 1963; vol. 41; pp. 103-106.
Lazar, H.L. et al. 'Novel Adhesive Skin Closures Improve Wound Healing Following Saphenous Vein Harvesting' J. Card Surg (2008) 23 pp. 152-155.
Leukosan SkinLink Application Guide (2006) 1 page.
Leukosan Skinlink. BSN Medical (2017) 1 page http://www.bsnmedical.com/products/wound%E2%80%90care%E2%80%90vascular/category%E2%80%90product%E2%80%90search/acute%E2%80%90wound%E2%80%90care/wound%E2%80%90closure/leukosanr%E2%80%90skinlink.html.
Pam Marketing Nut. Yikes! The Social Medica Quick Fix Band-Aids are Falling Off! Jul. 2012 [earliest online date], [site visited May 8, 2018]. Available from Internet, ,URL:http://www.pammarketingnut.com/2012/07/yikes-the-social-media-quick-fix-band-aids-are-falling-off/> (Year: 2012).
Parrish et al.: Synthetic resin adhesive for placement of skin grafts; *American Surgeon*; Nov. 1964; vol. 30; pp. 753-755.
Raekallio et al.: Acute reaction to arterial adhesive in healing skin wounds; *Journal of Surgical Research*; Mar. 1964; vol. 4; pp. 124-127.
Stone: Nonsuture closure of cutaneous lacerations, skin grafting and bowel anastomosis; *American Surgeon*; Mar. 1964; vol. 30; pp. 177-181.
TissuGlu Surgical Adhesive Patient Information Brochure. Cohera Medical, Inc. (2014) 6 pages.
TissuGlu FDA Summary of Safety and Effectiveness Data. Feb. 3, 2014 40 pages.
Topaz, M et al 'The TopClosure 3S System, for skin stretching and a secure wound closure' Eur J Plast Surg (2012) 35 pp. 533-543.
TopClosure 3S System—Skin Stretching and Secure Wound Closure System Product Information Sheet (2010) 15 pages.
Wang et al 'Biodegradable microfluidic scaffolds for tissue engineering from amino alcohol-based poly(ester amide) elastomers' Organogenesis (2010) 6:4, pp. 212-216.
Wolfe et al.: The application of hydrostatic pressure to the burn injury, an experimental study: *Journal of Trauma: Injury Infections & critical Care*; May 1962; vol. 2; pp. 262-272.
ZipLine medical Zip Surgical Skin Closure Brochure (2013) 4 pages.
Corrected International Search Report International Application No. PCT/US2005/004948 dated Jun. 22, 2005.
Extended European Search Report re: 14166813.7 dated Jul. 7, 2014.
International Preliminary Report on Patentability for International Application No. PCT/US2005/024042 dated Jan. 16, 2007.
International Search Report for International Application No. PCT/US2005/024042 dated May 12, 2006.
International Search Report for International Application No. PCT/US2005/004948 dated Jun. 9, 2009.
International Search Report re: PCT/US2015/051919 dated Apr. 14, 2016.
International Search Report re: PCT/US2017/052394 dated Nov. 21, 2017.
International Search Report re: PCT/US2017/052383 dated Dec. 6, 2017.
International Search Report re PCT/US2018/022842 dated Jun. 20, 2018.
International Search Report re PCT/US2018/022834 dated Jun. 22, 2018.
International Search Report re PCT/US2018/027790 dated Jun. 26, 2018.
Supplementary European Search Report for Application No. EP05769387 dated Jul. 9, 2009.

(56) References Cited

OTHER PUBLICATIONS

Supplementary European Search Report for Application No. EP05723162 dated Nov. 5, 2009.
Supplementary European Search Report for Application No. EP14166813 dated Jun. 30, 2014.
Written Opinion re: PCT/US2015/051919 dated Apr. 14, 2016.
Written Opinion re: PCT/US2017/052394 dated Nov. 21, 2017.
Written Opinion re: PCT/US2017/052383 dated Dec. 6, 2017.
Written Opinion re: PCT/US2018/022842 dated Jun. 20, 2018.
Written Opinion re: PCT/US2018/027790 dated Jun. 26, 2018.
Written Opinion re PCT/US2018/022834 dated Jun. 22, 2018.
Communication received from the USPTO for co-pending U.S. Appl. No. 10/887,884 dated Aug. 11, 2006.
Communication received from USPTO for co-pending U.S. Appl. No. 10/779,721 dated Mar. 28, 2007.
Communication received from USPTO for co-pending U.S. Appl. No. 10/779,721 dated Apr. 16, 2007.
Communication received from the USPTO for co-pending U.S. Appl. No. 10/887,884 dated Mar. 6, 2008.
Communication received from the USPTO for co-pending U.S. Appl. No. 10/887,884 dated Dec. 12, 2008.
Communication received from the USPTO for co-pending U.S. Appl. No. 12/207,984 dated May 11, 2011.
Communication received from the USPTO for co-pending U.S. Appl. No. 12/163,021 dated May 13, 2011.
Communication received from the USPTO for co-pending U.S. Appl. No. 12/163,021 dated Feb. 2, 2012.
Communication received from the USPTO for co-pending U.S. Appl. No. 12/163,021 dated Jun. 22, 2012.
Communication received from the USPTO for co-pending U.S. Appl. No. 12/207,984 dated Jun. 28, 2012.
Communication received from USPTO for co-pending U.S. Appl. No. 12/163,021 dated Jun. 22, 2012.
In re the U.S. Appl. No. 12/163,021 the Non-Final rejection dated Aug. 14, 2013.
In re the U.S. Appl. No. 12/163,021 the Final rejection dated Jan. 3, 2014.
In re the U.S. Appl. No. 12/207,984 the Non-Final rejection dated Aug. 22, 2013.
In re the U.S. Appl. No. 12/207,984 the Final rejection dated Dec. 4, 2013.
Office action received from USPTO for co-pending U.S. Appl. No. 10/887,884 dated Apr. 25, 2006.
Office action received from USPTO for co-pending U.S. Appl. No. 10/779,721 dated Aug. 21, 2006.
Office action received from USPTO for co-pending U.S. Appl. No. 10/887,884 dated Oct. 12, 2006.
Office action received from USPTO for co-pending U.S. Appl. No. 10/779,721 dated Jan. 9, 2007.
Office Communication received from USPTO for co-pending U.S. Appl. No. 10/887,884 dated Jan. 22, 2007.
Office Action received from USPTO for co-pending U.S. Appl. No. 10/887,884 dated Feb. 1, 2007.
Office Action received from the USPTO for co-pending U.S. Appl. No. 12/163,021.
Office action received from USPTO for co-pending U.S. Appl. No. 10/779,721 dated Jul. 27, 2007.
Office Action received from USPTO for co-pending U.S. Appl. No. 10/887,884 dated Oct. 16, 2007.
Office Action received from USPTO for co-pending U.S. Appl. No. 10/887,884 dated Mar. 6, 2008.
Office action received from USPTO for co-pending U.S. Appl. No. 10/779,721 dated May 19, 2008.
Office action received from USPTO for co-pending U.S. Appl. No. 12/163,021 dated Jan. 9, 2010.
Office action received from USPTO for co-pending U.S. Appl. No. 12/163,021 dated Sep. 1, 2010.
Office action received from USPTO for co-pending U.S. Appl. No. 12/207,984 dated Sep. 1, 2010.
Office action received from USPTO for co-pending U.S. Appl. No. 12/163,021 dated Dec. 9, 2010.
Office action received from USPTO for co-pending U.S. Appl. No. 12/207,984 dated Dec. 9, 2010.
Office action received from USPTO for co-pending U.S. Appl. No. 12/163,021 dated May 13, 2011.
Office action received from USPTO for co-pending U.S. Appl. No. 12/163,021 dated Jul. 18, 2011.
Office action received from USPTO for co-pending U.S. Appl. No. 12/207,984 dated Aug. 1, 2011.
Office action received from USPTO for co-pending U.S. Appl. No. 12/163,021 dated Jan. 10, 2012.
Office action received from USPTO for co-pending U.S. Appl. No. 12/207,984 dated Jan. 17, 2012.
Office action received from USPTO for co-pending U.S. Appl. No. 12/207,984 dated Apr. 26, 2012.
Office action received from USPTO for co-pending U.S. Appl. No. 12/163,021 dated May 1, 2012.
Office action received from USPTO for co-pending U.S. Appl. No. 12/163,021 dated Sep. 17, 2012.
Office action received from USPTO for co-pending U.S. Appl. No. 12/207,984 dated Sep. 25, 2012.
Office action received from USPTO for co-pending U.S. Appl. No. 12/163,021 dated Aug. 14, 2013.
Office action received from USPTO for co-pending U.S. Appl. No. 12/207,984 dated Aug. 22, 2013.
Office action received from USPTO for co-pending U.S. Appl. No. 12/207,984 dated Dec. 4, 2013.
Office action received from USPTO for co-pending U.S. Appl. No. 12/163,021 dated Jan. 3, 2014.
Office action received from USPTO for U.S. Appl. No. 15/964,538 dated Oct. 25, 2018.
Office action received from USPTO for U.S. Appl. No. 15/964,538 dated Dec. 27, 2018.
Office action received from USPTO for U.S. Appl. No. 15/490,176 dated Feb. 4, 2019.
Office action received from USPTO for U.S. Appl. No. 15/452,126 dated Nov. 16, 2018.
Office action received from USPTO for U.S. Appl. No. 14/864,033 dated Nov. 26, 2018.
Office action received from USPTO for U.S. Appl. No. 15/467,239 dated Feb. 28, 2019.
Office action received from USPTO for U.S. Appl. No. 15/278,376 dated Sep. 11, 2018.
Office action received from USPTO for U.S. Appl. No. 15/278,376 dated Feb. 21, 2019.
Office action received from USPTO for U.S. Appl. No. 15/675,159 dated May 14, 2019.
U.S. Appl. No. 09/430,177, filed Oct. 29, 1999.
U.S. Appl. No. 09/430,289, filed Oct. 29, 1999.
U.S. Appl. No. 09/430,180, filed Oct. 29, 1999.
U.S. Appl. No. 09/385,030, filed Aug. 30, 1999.
U.S. Appl. No. 09/176,889, filed Oct. 22, 1998.
U.S. Appl. No. 09/919,877, filed Aug. 2, 2001.
U.S. Appl. No. 10/779,721, filed Feb. 18, 2004.
N/A, "Scar nose & Rinoplasty Surgery—New Gel+Demo:Nose Silicone Gel Sheet (beige)www.newgelplus.com", www.youtube.com, 2012, pp. 1-3, Page Number.
N/A, "Silagen Silicone Sheeting Strips Review|the skin spot", www.youtube.com, 2017, pp. 1-3, Page Number.

\* cited by examiner

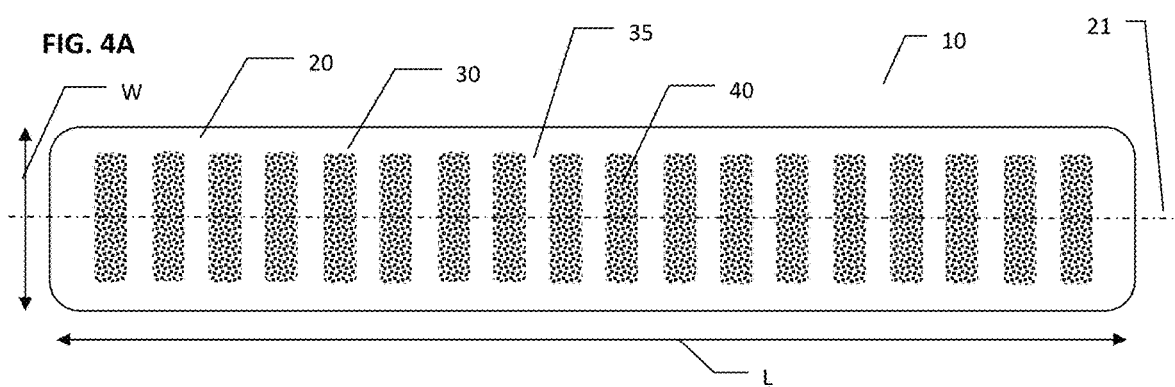
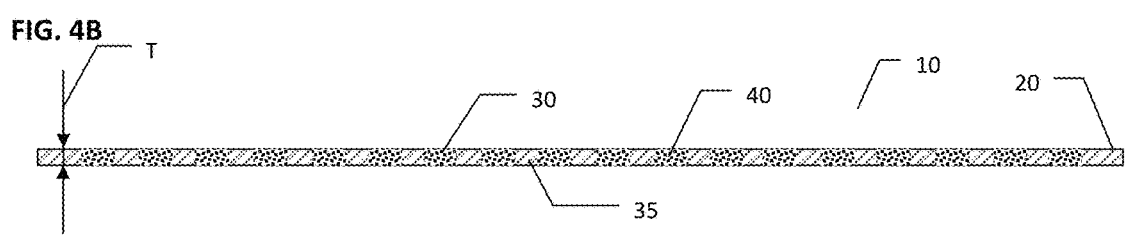

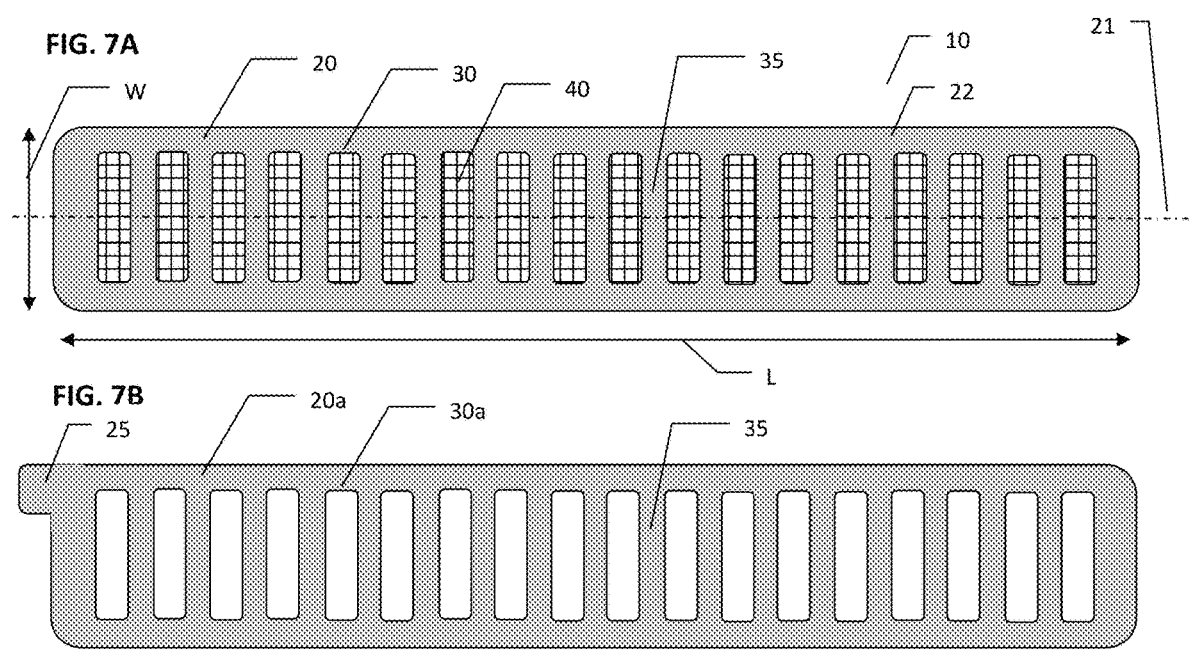

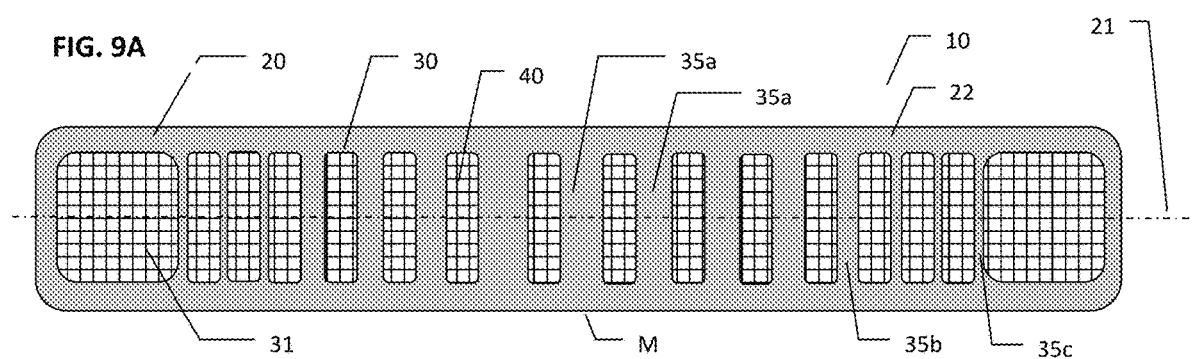
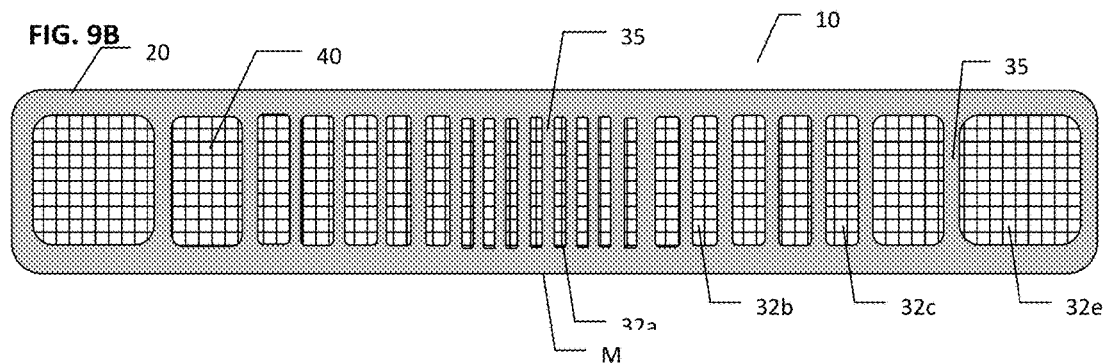

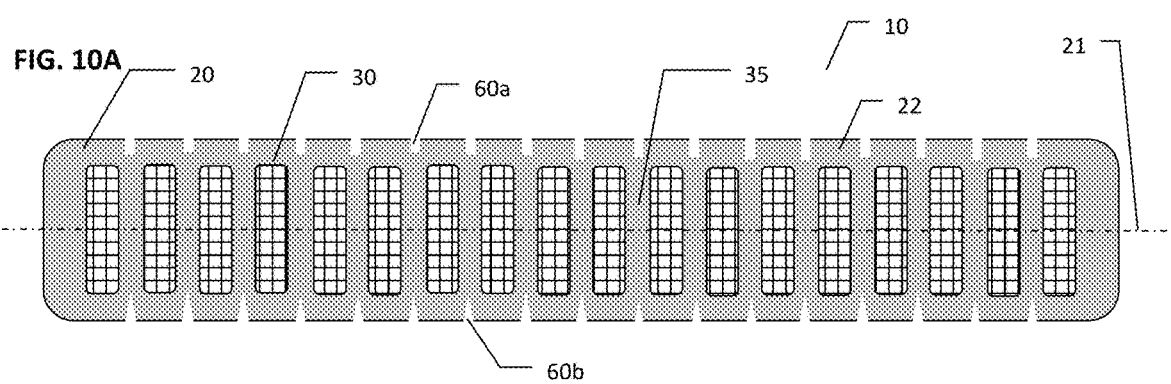
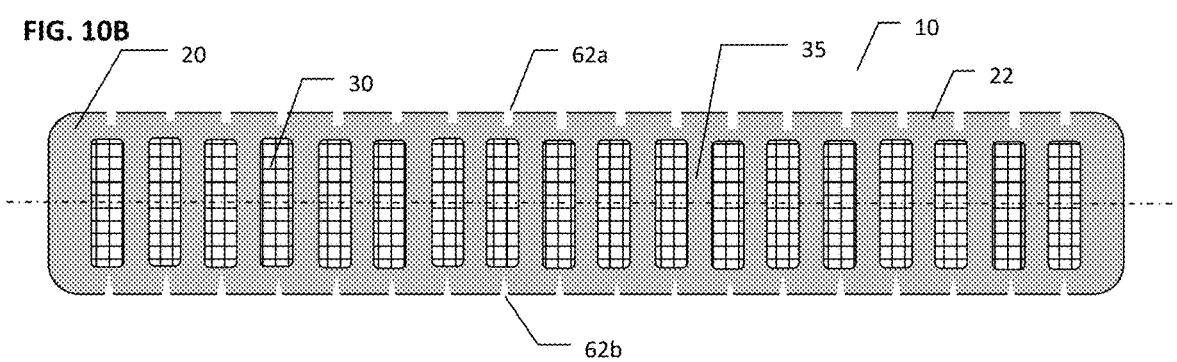

SKIN CLOSURE SYSTEMS AND DEVICES OF IMPROVED FLEXIBILITY AND STRETCHABILITY FOR BENDABLE JOINTS

The present disclosure relates to skin closure systems and devices comprising elastic flat flexible tape elongated along a main axis and having a lower side and an opposing upper side, said tape having a pressure sensitive adhesive on at least a portion of the lower side, said tape having a plurality of openings arranged side-by-side with spaces between said openings oriented across the main axis. Skin closure device is applied over a surgical incision and secured by polymerizable adhesive.

BACKGROUND

A number of devices and methods exist for closing skin or tissue having a surgical opening, cut, wound, or dissection, whereby skin or tissue parts separated by the cut are approximated or brought into close proximity forming as narrow gap as possible in the area of the surgical dissection or cut, and then covered by an adhesively attached tape which holds the skin or tissue in closed apposed arrangement until wound healing whereby the tape is removed.

Commercially available DERMABOND® PRINEO® Skin Closure System comprises a mesh having a pressure sensitive adhesive and a polymerization initiator disposed on the mesh. The mesh is applied onto the skin over a wound, and a polymerizable cyanoacrylate based adhesive is then applied on the mesh and bonds the mesh to the skin. However, skin closure systems, such as DERMABOND® PRINEO® Skin Closure System, may benefit from more stretching for flexibility/joint articulation if applied over a joint, such as knee, elbow, or similar, while holding the dissection applied lengthwise or longitudinally along the joint.

A number of attempts to address this issue are known, including commercial products: such as TopClosure® 3S System—Skin Stretching and Secure Wound Closure System; Steri-Strip™ by 3M™; Zip®16 Surgical Skin Closure by Zipline Medical. These known systems are complex and either lack flexibility or lack secure and lasting bonding and coverage which extends for the time needed for full healing, such as 1-2 weeks.

PCT publication No. WO2008/082444 titled "Articles and Methods for Tissue Repair" discloses a method of medically treating a tissue comprising: directing a transfer device to a tissue surface, the transfer device having associated therewith a patterned array of an adhesive; transferring at least a portion of the patterned array of adhesive from the transfer device to the tissue surface by contact adhesion; moving the transfer device away from the tissue surface; positioning an article to be adhered adjacent at least a portion of the adhesive; and adhering the article to the tissue surface using the adhesive.

U.S. Pat. No. 8,353,966 entitled "Scaffold for Bone and Tissue Repair in Mammals" discloses a tissue scaffold for repair and regeneration of bone hard tissue or muscle, skin, or organ soft tissue, the scaffold comprising: a rigid scaffold body having a scaffold central axis, a scaffold transverse dimension, and a scaffold lengthwise dimension which is greater than the scaffold transverse dimension, the scaffold body having a compressive strength between about 20 and about 250 MPa and comprising: biocompatible inorganic glass fibers each having a fiber transverse dimension and a fiber lengthwise dimension which is at least about 10 times the fiber transverse dimension; and an interconnected porosity constituting between about 10 vol. % and about 35 vol. % of the scaffold body; wherein each of the fibers has a diameter between about 20 and about 5000 microns; wherein at least about 75 vol. % of the fibers are longitudinally co-aligned and lie generally lengthwise of the scaffold central axis, are generally free of helical orientation about the scaffold central axis, and are arranged to define open channels within the scaffold which allow fluid flow into and lengthwise within the scaffold; and wherein the fibers are self-bonded together in that adjacent longitudinally aligned fibers are fused together.

U.S. Pat. No. 6,652,559 entitled "Wound Closure System" discloses a wound closure system for closing a wound on a patient, comprising: an elongated flexible backing strip having opposite ends, first and second surfaces facing away from one another and a length and width sufficient to secure facing edges of the wound in close juxtaposition to one another, said backing strip comprising a first portion disposed between said ends and adapted to overlie the facing edges of said wound, and second and third portions disposed on either side of said first portion and each provided with a predetermined number of spaced-apart perforations extending through said backing strip from said first surface to said second surface, said first portion being free of any aperture extending through said backing strip from said first surface to said second surface; a first pressure-sensitive adhesive coated on at least part of the first surface of said backing strip including said second and third portions thereof, to adhere at least said second and third portions of said backing strip to the patient with the facing edges of said wound in said close juxtaposition; a first protective member removably attached to said backing strip and covering said pressure-sensitive adhesive; and a flowable, moisture-curable surgical adhesive for application into said perforations to strengthen the adhesion of said second and third portions of said backing strip to the patient; whereby after (a) removal of said protective member to expose said pressure-sensitive adhesive, (b) application of said backing strip with the exposed pressure-sensitive adhesive onto said patient to secure the facing edges of said wound in said close juxtaposition, and (c) application of said surgical adhesive into said apertures, said surgical adhesive flows through said perforations and upon curing forms discrete bonding sites cooperating with said backing strip to maintain the facing edges of said wound in said close juxtaposition without the cured adhesive adversely affecting the flexibility of said backing strip, wherein a second protective member having a second pressure-sensitive adhesive coated on one side thereof is removably attached to said backing strip and covers said second surface, said strip being disposed between said first and second protective members, and wherein said second protective member is provided with a corresponding number of perforations registering with the perforations defined in said second and third portions of said backing strip, and being in flow communication therewith.

U.S. Pat. No. 6,559,350 entitled "MOISTURE-CURABLE ADHESIVE SUTURE STRIP" discloses a moisture-curable adhesive suture strip for closing a wound on a patient, comprising: an elongated, flexible air-permeable backing member formed of a chemically inert material, and having opposite ends, first and second surfaces facing away from one another and a length and width adapted to secure facing edges of the wound in close juxtaposition to one another, said backing member comprising a first portion disposed between said ends and adapted to overlie the facing edges of said wound, and second and third portions disposed on either side of said first portion; a moisture-curable surgical adhesive on at least part of the first surface of said backing member including said second and third portions thereof, in spaced-apart discrete areas of said first surface; a pressure-sensitive adhesive on the first surface of said backing member between said discrete areas for adhering at least said second and third portions of said backing member to the patient with the facing edges of said wound in said close juxtaposition; and a first removable protective member formed of a chemically inert material releasably secured to said backing member and covering said surgical adhesive and said pressure-sensitive adhesive; whereby after removal of said protective member to expose said surgical adhesive and said pressure sensitive adhesive, and application of said backing member with the exposed surgical adhesive pressure sensitive adhesive onto said patient to secure the facing edges of said wound in said close juxtaposition, said surgical adhesive upon curing forms discrete bonding sites strengthening the adhesion of at least said second and third portions of said backing member to the patient and cooperating with said backing member to maintain the facing edges of said wound in said close juxtaposition without the cured adhesive adversely affecting the flexibility of said backing member.

U.S. Patent Application Publication No. 2013/0012988 entitled "Wound Closure Material" discloses wound closure material with a core of biodegradable material, wherein at least one side of the core of biodegradable material is provided with a multitude of discrete spots of an adhesive and the core of biodegradable material comprises an open cell structure.

U.S. Pat. No. 8,642,831 entitled "Device for Promotion of Hemostasis and/or Wound Healing" discloses a hemostatic matrix material comprising a surface and a plurality of open and interconnected cells, said matrix material comprising gelatine or collagen, wherein the surface of said matrix comprises at least one pharmaceutical composition printed onto said surface in individual and discrete locations, wherein said pharmaceutical composition comprises one or more hemostatic agents.

U.S. Patent Application publication No. 2014/0155916 entitled "Multi-layer Porous Film Material" discloses a surgical implant, comprising: a first porous film layer including a plurality of pores; and a second porous film layer including a plurality of pores, the first and second porous film layers being in a stacked configuration and interconnected to one another at a plurality of attachment points to define at least one void between the first and second porous film layers.

U.S. Patent Application publication No. 2008/0109034 entitled "Controlled Adhesive Locations Facilitating Tissue Remodeling" discloses a surgical implant for adhering two portions of tissue together comprising; a) an implantable matrix having at least one layer and a plurality of openings formed within the at least one layer for tissue growth therethrough; and b) a polymer adhesive about the implantable matrix for adhering the two portions of tissue together, the adhesive polymerizing to adhere the tissue together when the two portions of tissue are brought together.

U.S. Patent Application publication No. 2006/0141012 entitled "Tissue Scaffold" discloses a tissue scaffold comprising: a first film including a plurality of cell openings; and a second film adjacent the first film and including a plurality of cell openings larger than the cell openings of the first film; wherein the cell openings of the first film interconnect with the cell openings of the second film to define pathways extending from the first film to the second film.

U.S. Patent Application publication No. 2013/0204077 entitled "Surgical Scaffolds" discloses a surgical scaffold for soft tissue repair, said surgical scaffold comprising a sheet of non-filamentous polymeric material, at least a portion of the sheet surface comprising a plurality of through-holes.

Leukosan® SkinLink by BSN Medical and distributed by Smith and Nephew Pty Ltd, has an apertured band-aid like structure.

Synthetic tissue adhesive TissuGlu® Surgical Adhesive by Cohera Medical, Inc. is based on a polyurethane prepolymer and is applied in a spot-like discrete application of the adhesive during abdominoplasty, using a multi-point dispenser.

Very flexible and elastic tapes will allow for joint flexibility, but will not hold the skin areas in apposed arrangement due to the same elasticity, potentially resulting in wound dehiscence or surgical complication in which a wound ruptures along a surgical incision. Other known systems fail to fully cover the wound resulting in potential for ingress of contaminants and infection causing microorganisms. Other known systems are overly rigid preventing articulation or bending of the joint.

There continues to be a need for improved devices, systems, and methods for holding skin areas around the dissection in apposed arrangement while still providing for flexibility in longitudinal direction enabling bending of the underlying joints.

SUMMARY OF THE INVENTION

In one embodiment, a device for skin closure comprises an elastic flat flexible tape elongated along a main axis and having a lower side and an opposing upper side, said tape having a pressure sensitive adhesive on at least a portion of the lower side, said tape having a plurality of openings arranged side-by-side with spaces between said openings oriented across the main axis.

According to another embodiment, there is provided a method of skin closure, comprising the steps of disposing the device onto skin having a surgical incision with the main axis approximately aligned with the surgical incision; apposing and approximating edges of the incision to each other; using the pressure sensitive adhesive to fixate the device on skin; applying a polymerizable adhesive onto the upper side into the openings; Allowing the polymerizable adhesive to polymerize and bond to skin and to the device; rendering the device substantially not stretchable in the directions perpendicular to the main axis but stretchable along the main axis providing for flexibility and enabling bending of underlying joints; providing coverage of the incision and keeping the incision closed.

BRIEF DESCRIPTION OF THE DRAWINGS

FIGS. 4A-B show an embodiment of the skin closure device in a schematic top view and cross-sectional side view.

FIGS. 7A-B show embodiments of the skin closure device in schematic top views.

FIGS. 9A-B show embodiments of the skin closure device in schematic top views.

FIGS. 10A-B show embodiments of the skin closure device in schematic top views.

DETAILED DESCRIPTION

Figure 1A:
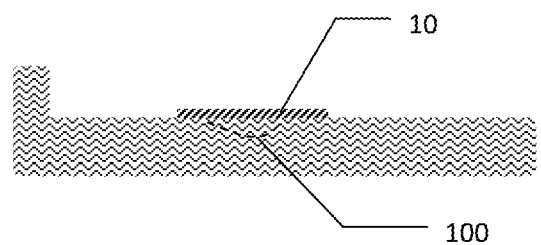
FIGS. 1A-D show applications of an embodiment of the device of the skin closure system to a joint in schematic side and top views.
Figure 1B:
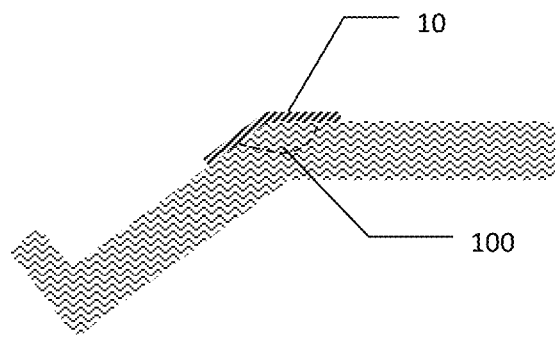
Figure 1C:
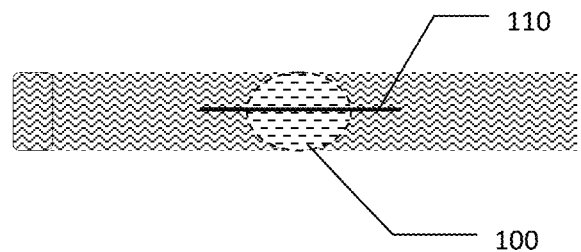
Figure 1D:
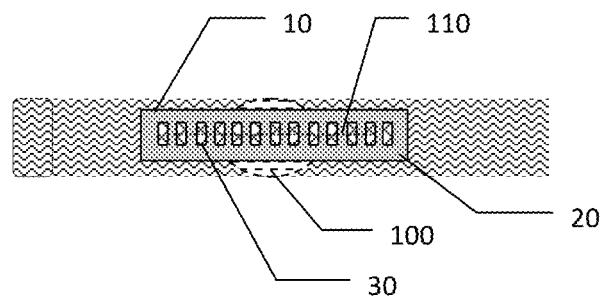

Referring now to FIG. 1, a schematic cross-sectional view of a joint 100, such as knee or elbow (knee is shown), with an embodiment of device 10 applied over the joint 100, which is not bent, as seen in FIG. 1A, or bent as shown in FIG. 1B. FIG. 1C shows joint 100 in top view, with the surgical incision or wound 110 present and directed along the limb having joint 100. FIG. 1D shows joint 100 in top view, with an embodiment of device 10 of the present invention applied to joint 100 and fully covering surgical incision or wound 110. Device 10 is elongated and applied along the limb having joint 100 and along surgical incision or wound 110.

Referring now to FIG. 2, embodiments of Skin Closure System device 10 are shown, with device 10 comprising a thin, flat, flexible and elastic tape 20 having length L and width W and elongated along axis 21, with upper side 22 and lower side 23, with tape 20 having a plurality of openings 30 each spanning a large portion of the width W of tape 20 or the whole width W (as shown, e.g., in FIG. 3), with openings 30 arranged side by side along the length L and separated by spacer areas 35. Openings 30 are fully covered by porous mesh 40 preferably having an initiator or accelerator of polymerization disposed on the mesh 40, coated on the mesh 40, and/or impregnated into the mesh 40. Preferably, initiator or accelerator of polymerization is disposed, coated, or impregnated onto/into at least openings 30 or mesh present in opening 30, or onto whole tape 20.

Figure 2A:
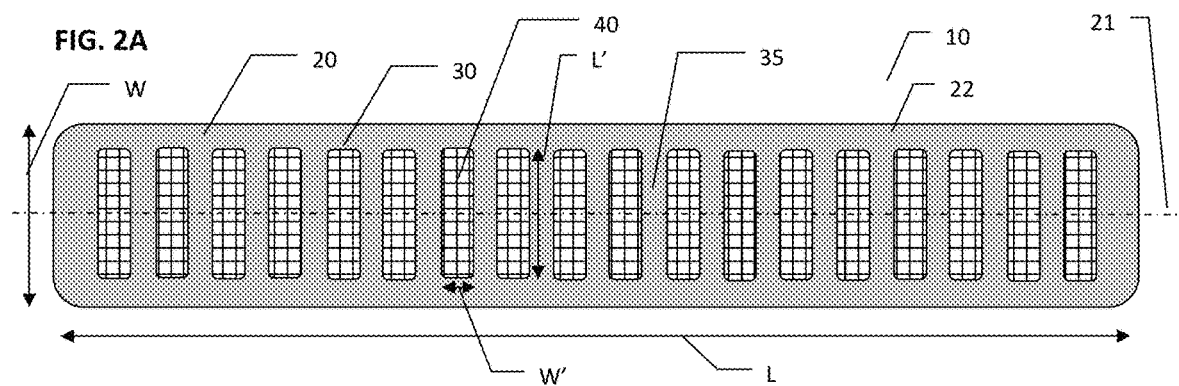
FIGS. 2A-E show embodiments of the skin closure device in schematic top view and cross-sectional side views.
Figure 2B:
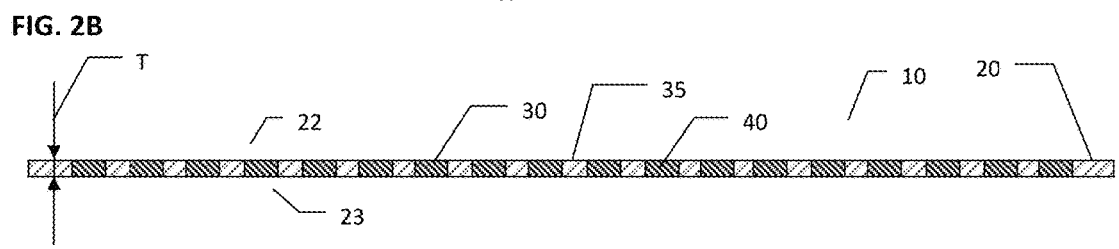
Figure 2C:
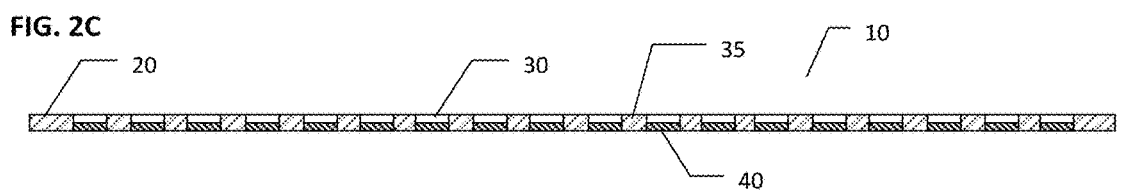
Figure 2D:
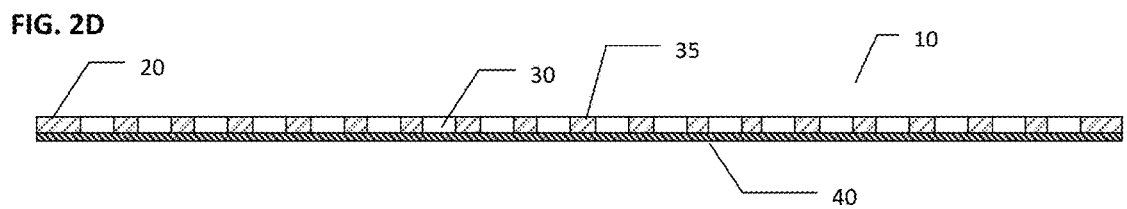

FIG. 2A shows the top view of device 10 while FIGS. 2B, 2C, 2D show cross-sectional views of different constructions corresponding to top view 2A. According to an embodiment of device 10 shown in FIG. 2B, mesh 40 has the thickness similar to thickness T of tape 20, with mesh present within openings 30. As used herein, the term "present" means that the mesh is exposed or disposed or positioned within openings 30. According to an embodiment of device 10 shown in FIG. 2C, mesh 40 has thickness which is lower than thickness T of tape 20, with mesh present within openings 30. According to an embodiment of device 10 shown in FIG. 2D, mesh 40 is disposed on a lower surface of tape 20.

Mesh 40 alternatively can be a porous nonwoven, felt, porous woven fabric, textile, foam, or similar. Mesh 40 can also be an extruded film porated during or after extrusion or formed directly with apertures.

Figure 2E:
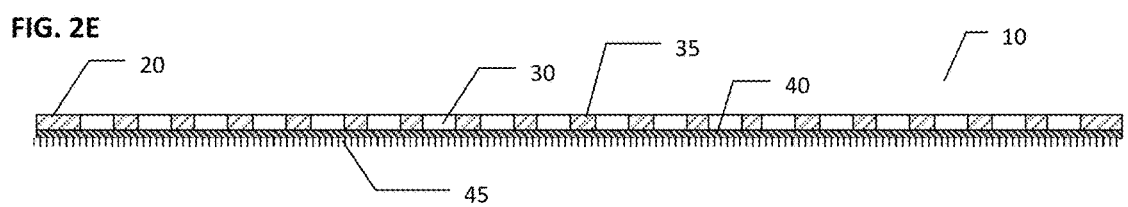

Tape 20 is made of a polymeric flexible and elastic material. Elastic property is defined by stretchability at least in the lengthwise direction, with stretchability from 1% to 50% of length when exposed to 1 N of force, more preferably 3%-25% of the initial or unstressed length. The 'elastic' property is a function of the material from which the mesh is constructed and/or the nature of the mesh construction itself. Mesh 40 is made of flexible material, which can optionally also be elastic. Mesh 40 can be polymeric, metal, ceramic, natural fiber, etc., with preferable material being polymeric. Lower side 23 has optionally a pressure sensitive adhesive (PSA) disposed thereon, which can cover the whole lower side 23, or only a portion of lower side 23 in any pattern. In one embodiment, PSA is applied in equally spaced stripes across whole lower side 23. In another embodiment, PSA is applied only on the areas free of openings 30 on lower side 23. In another embodiment, PSA is applied only on the areas where openings 30 are present on lower side 23 and optionally above and below openings 30. In yet another embodiment, PSA is applied uniformly everywhere on lower side 23. FIG. 2E shows PSA 45 disposed on tissue facing or wound facing lower side 23. PSA can be on tape 20 and/or on mesh 40.

In use and referring to FIG. 2, device 10 is disposed on tissue or skin having a wound with axis 21 approximately aligned with the surgical incision or wound, with the edges of the incision apposed and approximated to each other. A polymerizable adhesive is then applied onto upper side 22, onto the whole upper side 22 surface or more preferably only onto/into openings 30 on upper side 22. If an initiator or accelerator is present, the polymerizable adhesive reacts with the initiator or accelerator of polymerization disposed on the mesh 40, coated on the mesh 40, and/or impregnated into the mesh 40 resulting in polymerization and bonding of the adhesive to the skin or tissue in the areas corresponding to openings 30 and to the device 10. Bonding to device 10 is at least in part due to bonding to mesh 40 disposed within openings 30.

The application of adhesive results in device 10 being bonded to the skin and covering the wound or incision while holding skin areas around the dissection in apposed arrangement. Due to presence of the adhesive, device 10 is substantially not stretchable in the directions perpendicular to axis 21, keeping the wound or incision closed and skin areas around the dissection in apposed arrangement. At the same time device 10 is stretchable along the main axis providing for flexibility in longitudinal direction enabling bending of the underlying joints, while also providing coverage of the wound or incision. Advantageously, wound dehiscence or surgical complication in which a wound ruptures along a surgical incision is therefore prevented, while also fully covering the wound and enabling articulation or bending of the joint.

Figure 3A:
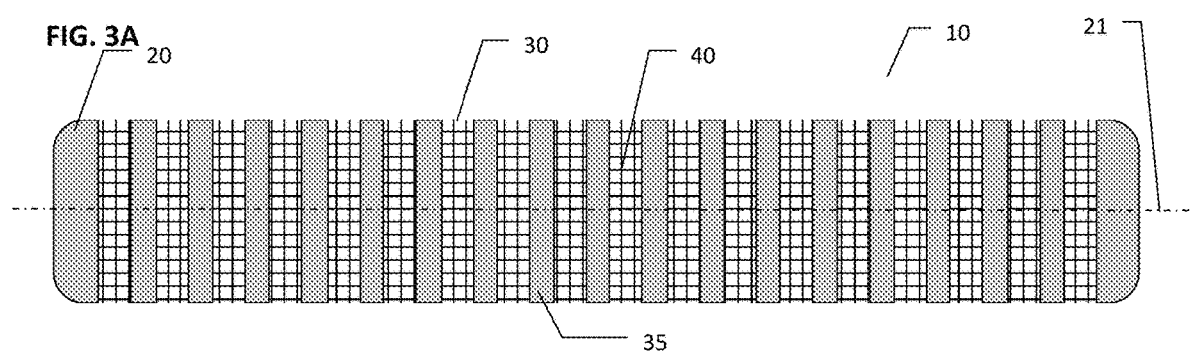
FIGS. 3A-B show embodiments of the skin closure device in a schematic top view and a cross-sectional side view.
Figure 3B:
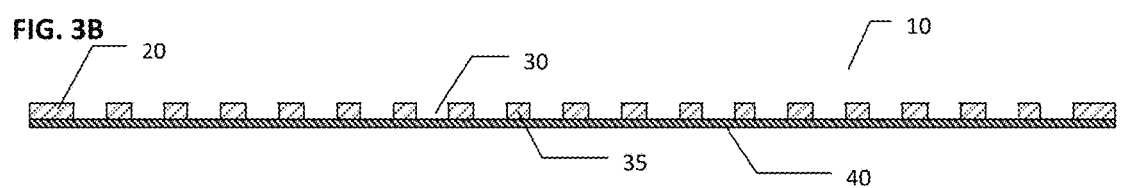

Referring now to FIGS. 3A and 3B, embodiments of Skin Closure System device 10 similar to the embodiments of FIG. 2 are shown, with plurality of openings 30 each spanning the whole width of tape 20, with openings 30 arranged side by side along the length of tape 20 and separated by spacer areas 35. According to an embodiment of device 10 shown in FIG. 3B showing a cross-sectional view, mesh 40 is disposed on a lower surface of tape 20.

According to an embodiment (not shown), there is provided a kit, comprising device 10, a container containing a polymerizable or cross-linkable liquid adhesive, and a dispenser adapted to dispense adhesive. In one embodiment, dispenser has a tip for expressing the polymerizable adhesive, wherein the tip has a width equal to a width of openings 30.

Referring now to FIGS. 4A and 4B, embodiments of Skin Closure System device 10 similar to the embodiments of FIGS. 2,3 are shown, but with openings 30 comprising areas of porated or perforated tape 20, with no mesh 40 used to form device 10 of this embodiment. Preferably, initiator or accelerator of polymerization is disposed, coated, or impregnated onto/into at least openings 30 comprising areas of porated or perforated tape 20 or onto whole tape 20.

No Mesh

Figure 5:
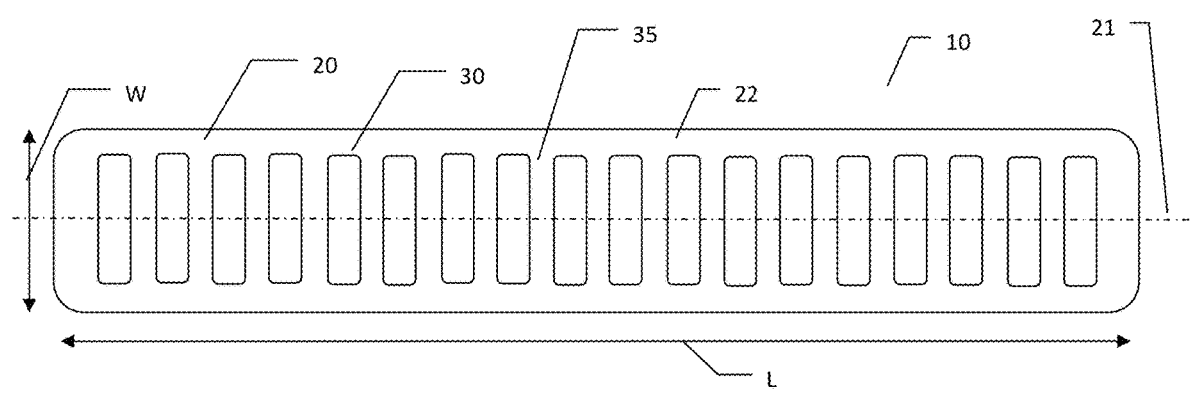
FIG. 5 shows an embodiment of the skin closure device in a schematic top view.

Referring now to FIG. 5, an embodiment of Skin Closure System device 10 similar to the embodiments of FIGS. 2, 4 are shown, but with openings 30 comprising areas of material removed from tape 20, with no pores or mesh within openings 30, i.e., openings 30 comprising cut-outs or holes with no material disposed within openings 30. In use, this embodiment is preferably utilized with an adhesive dispenser which has initiator or accelerator of polymerization admixed into the adhesive upon dispensing, such as from a porous tip impregnated with initiator or accelerator of polymerization.

In use and referring to FIG. 5, device 10 is disposed on tissue or skin having a wound with axis 21 approximately aligned with the surgical incision or wound, with the edges of the incision apposed and approximated to each other. A polymerizable adhesive is then applied onto upper side 22 onto the whole upper side 22 surface or more preferably only onto/into openings 30 on upper side 22. The polymerizable adhesive is dispensed from a porous tip impregnated with initiator or accelerator of polymerization, reacts with the initiator or accelerator of polymerization, if present, resulting in polymerization and bonding of the adhesive to the skin or tissue in the areas corresponding to openings 30 and to the device 10. The application of adhesive results in device 10 being bonded to the skin or tissue in the areas corresponding to openings 30 and covering the wound or incision while holding skin areas around the dissection in apposed arrangement. Due to presence of the adhesive, device 10 is substantially not stretchable in the directions perpendicular to axis 21, keeping the wound or incision closed and skin areas around the dissection in apposed arrangement. At the same time device 10 is stretchable along the main axis providing for flexibility in longitudinal direction enabling bending of the underlying joints.

Mask

Figure 6A:
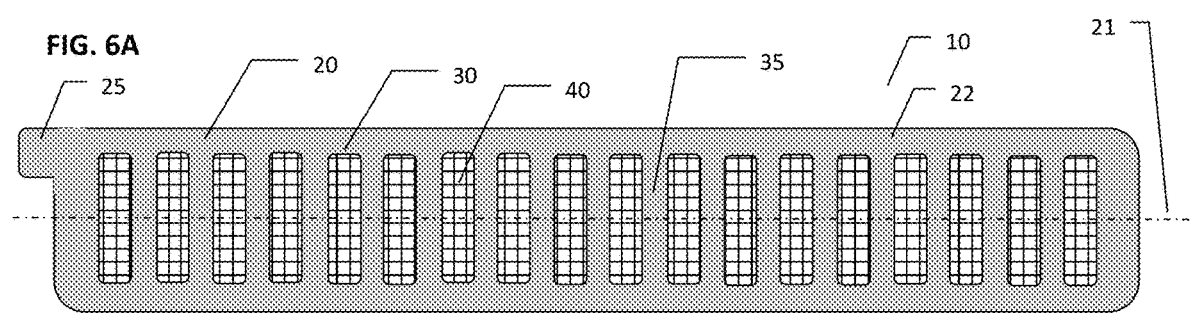
FIGS. 6A-C show embodiments of the skin closure device in schematic top views.
Figure 6B:
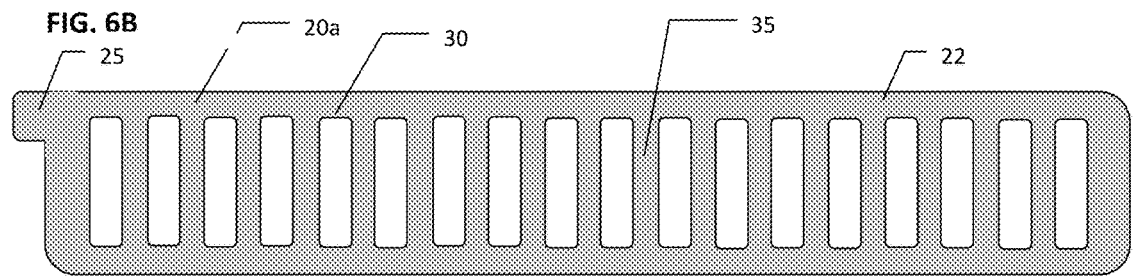
Figure 6C:
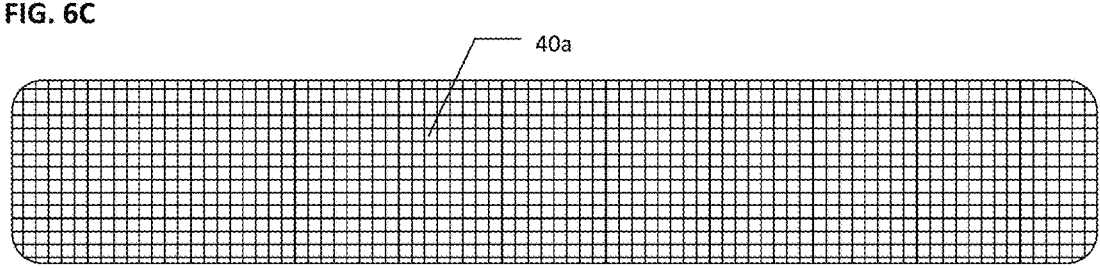

Referring now to FIG. 6, an embodiment of Skin Closure System device 10 similar to the embodiments of FIGS. 2A, 2D is shown. FIG. 6A shows assembled device 10 which comprises tape 20a shown in FIG. 6B, representing a removable mask 20a which is made of a polymeric flexible material which can be optionally non-elastic or elastic, with mask 20a releasably disposed on mesh 40a shown in FIG. 6C, with mesh 40a made of polymeric flexible and elastic material. Mask 20a is attached to mesh 40 with a weak PSA disposed on mask 20a (not shown) or by a compression fit or by any other method known in the art assuring easy release of mask 20a from mesh 40a. Optional one or more tabs 25 are provided for easy lift-off and removal of mask 20a. In an alternative embodiment (not shown) mask 20a is larger than mesh 40a and the edges of mask 20a can be used as tabs 25.

In operation, assembled device 10 is disposed on tissue or skin having a wound with axis 21 approximately aligned with the surgical incision or wound, with the edges of the incision apposed and approximated to each other. A polymerizable adhesive is then applied onto upper side 22, onto the whole upper side 22 surface or more preferably only onto/into openings 30 on upper side 22. Mask 20a is then removed and discarded. All of the excess adhesive is removed on mask 20a. The polymerizable adhesive reacts with the initiator or accelerator of polymerization if disposed on the mesh 40, if coated on the mesh 40, and/or if impregnated into the mesh 40 resulting in polymerization and bonding of the adhesive to the skin or tissue and to mesh 40 in the areas of mesh 40 corresponding to openings 30. The application of adhesive results in mesh 40 being bonded to the skin and covering the wound or incision while holding skin areas around the dissection in apposed arrangement. Due to presence of the adhesive, mesh 40 is substantially not stretchable in the directions perpendicular to axis 21, keeping the wound or incision closed and skin areas around the dissection in apposed arrangement. At the same time device 10 is stretchable along the main axis providing for flexibility in longitudinal direction enabling bending of the underlying joints.

Referring now to FIG. 7, an embodiment of Skin Closure System device is shown which is a combination of the device 10 of embodiments of FIG. 2A or 4 (shown in FIG. 7A) with mask 20a (shown in FIG. 7B) of embodiment of FIG. 6 is shown. Skin Closure System device, in this embodiment, comprises a combination of device 10 of embodiment 2A or 4 comprising tape 20 having a plurality of openings 30 as shown in FIG. 7A with removable mask 20a which is shown in FIG. 7B having openings 30a which have substantially similar dimensions and positions and are in registration with openings 30 on device 10. Mask 20a is then releasably disposed on device 10 upper side 22 and can be attached with a weak PSA disposed on mask 20a or by a compression fit or by any other method known in the art assuring easy release of mask 20a, with openings 30a in registration with openings 30. Optionally, one or more tabs 25 are provided for easy lift-off and removal of mask 20a. In an alternative embodiment (not shown) mask 20a is larger than mesh 40a and the edges of mask 20a can be used as tabs 25.

In operation, assembled Skin Closure System device with device 10 with mask 20a disposed on upper side 22 is disposed on tissue or skin having a wound with axis 21 approximately aligned with the surgical incision or wound, with the edges of the incision apposed and approximated to each other. A polymerizable adhesive is then applied onto mask 20a surface or more preferably only onto/into openings 30 and 30a. Mask 20a is then removed and discarded. All of the excess adhesive is removed on mask 20a. The polymerizable adhesive reacts with the initiator or accelerator of polymerization if disposed on the mesh 40, if coated on the mesh 40, and/or if impregnated into the mesh 40 resulting in polymerization and bonding of the adhesive to the skin or tissue and to mesh 40 in the areas of mesh 40 corresponding to openings 30. The application of adhesive results in mesh 40 being bonded to the skin and covering the wound or incision while holding skin areas around the dissection in apposed arrangement. Due to presence of the adhesive, mesh 40 is substantially not stretchable in the directions perpendicular to axis 21, keeping the wound or incision closed and skin areas around the dissection in apposed arrangement. At the same time device 10 is stretchable along the main axis providing for flexibility in longitudinal direction enabling bending of the underlying joints.

Separate Openings

Figure 8A:
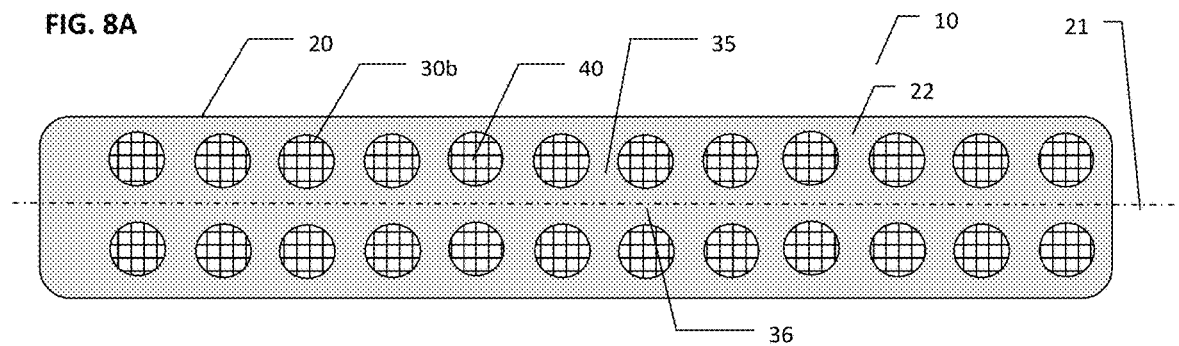
FIGS. 8A-C show embodiments of the skin closure device in schematic top views.
Figure 8B:
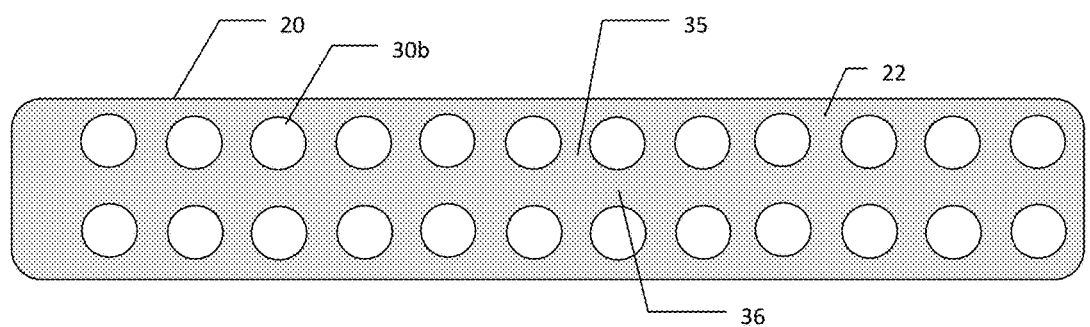

Referring now to FIG. 8, an embodiment of Skin Closure System device 10 is shown, with device 10 comprising a thin, flat, flexible and elastic tape 20 elongated along axis 21, with tape 20 having a plurality of openings 30b arranged side by side along the length L and separated by longitudinal spacer areas 35 and further arranged above and below axis 21 and separated by axial spacer areas 36, with no openings 30b overlapping axis 21. As shown in FIG. 8A, in one embodiment, openings 30b are fully covered by porous mesh 40 with mesh 40 preferably having an initiator or accelerator of polymerization disposed on the mesh 40, coated on the mesh 40, and/or impregnated into the mesh 40. In an alternative embodiment shown in FIG. 8B, openings 30*b* have no mesh disposed within the openings, i.e. openings 30*b* are comprising cut-outs or holes with no material disposed within openings 30*b*. Tape 20 is made of a polymeric flexible and elastic material. Mesh 40 is made of polymeric flexible material, which can optionally also be elastic. Lower side 23 has optionally a pressure sensitive adhesive (PSA) disposed thereon, which can cover the whole lower side 23, or only a portion of lower side 23 in any pattern.

Figure 8C:
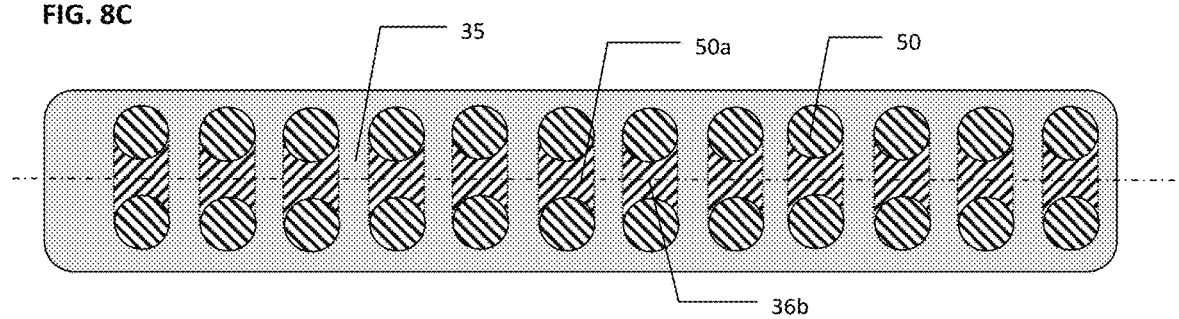

In use, device 10 is disposed on tissue or skin having a wound with axis 21 approximately aligned with the surgical incision or wound, with the edges of the incision apposed and approximated to each other. A polymerizable adhesive 50 is then applied onto upper side 22, or more preferably only onto/into openings 30*b* on upper side 22 and onto axial spacer areas 36 formed between openings 30*b* opposing each other across axis 21, as shown in FIG. 8C. The polymerizable adhesive polymerizes resulting in bonding of adhesive 50 to the skin or tissue and to the device 10. Simultaneously, a portion of adhesive 50*a* coated on upper side 22 between openings 30*b* axial spacer areas 36 forms areas of lesser stretchability and higher rigidity 36*b* between openings 30*b* opposing each other across axis 21, as shown by hatched line shadowing in FIG. 8C. Portions of adhesive 50 and 50*a* can polymerize due to initiator if disposed on mesh 40, and/or on upper side of tape 20, and/or on upper side of tape 20 in axial spacer areas 36 between openings 30*b*. With regards to the embodiment shown in FIG. 8B, whereby openings 30*b* have no mesh disposed within the openings, the polymerizable adhesive can be dispensed from a porous tip impregnated with initiator or accelerator of polymerization, whereby adhesive reacts with the initiator or accelerator of polymerization, resulting in polymerization and bonding of the adhesive to the skin or tissue and to the device 10.

The application of adhesive results in device 10 being bonded to the skin and covering the wound or incision while holding skin areas around the dissection in an apposed arrangement and thereby forming a composite of the device with the polymerized adhesive. Due to presence of the adhesive, device 10 is substantially not stretchable in the directions perpendicular to axis 21, keeping the wound or incision closed and skin areas around the dissection in apposed arrangement. At the same time device 10 is stretchable along the main axis providing for flexibility in longitudinal direction enabling bending of the underlying joints, while also providing coverage of the wound or incision. Advantageously, in the embodiments of FIG. 8, no adhesive is in direct contact with the surgical cut or wound area, which area is positioned substantially aligned with axis 21 and under axial spacer areas 36 between openings 30*b*, resulting in no contact of adhesive with cut tissue.

Variable Width

Referring now to FIG. 9A, an embodiment of Skin Closure System device 10 is shown, with openings 30 separated by spacers of varying width, whereby in the middle M of device 10 spacer areas 35*a* are wider and towards the ends spacer areas 35*b* are narrower, and close to the ends spacer areas 35*c* are narrowest. This results in more stretchability around the center or middle M of device 10 as stretchability is defined by spacer areas 35. Optionally, openings 30 become wider further from the center of middle M and close to the ends of device 10, as shown by openings 31 which are about 2-3 times wider than openings 30 which are closer to the middle. This results in more stretchability around the center or middle M of device 10.

Referring now to FIG. 9B, an embodiment of Skin Closure System device 10 is shown, with openings in tape 20 having variable width, with openings 32*a* narrowest in the middle M of device 10, openings 32*b*, 32*c* wider towards the ends of the devices, and with openings 32*e* close to the end of the device 10 being widest, such as 2-10 times wider vs. openings 32*a*. This results in more stretchability around the center or middle M of device 10. Spacer areas 35 can be of uniform width, as shown, or of varying width (not shown) similar to presented in FIG. 9A.

Slits

Referring now to FIG. 10, embodiments of Skin Closure System device 10 are shown, with slits 60 cut into periphery of tape 20. Slits 60 can be of any shape, such as rectangular cuts 60*a* or triangular cuts 60*b*. Slits 60 can be cut into periphery of tape 20 in the areas between openings 20, as shown in FIG. 10A, or be aligned with openings 30, as shown in FIG. 10B. Slits 60 penetrate tape 20 for about 3% to about 20% of the width W of tape 20, but in no case slits 60 penetrate into openings 30. Slits 60 provide for more stretchability of device 10. Slits 60 also allow for some lateral bending of device 10 for non-linear incisions. In some embodiments (not shown) slits 60 are only present around center or middle M of tape 20. Slits 60 can also be just on one side of device 10.

Shapes

In one embodiment, the width W of the device varies along the axis 21. In one embodiment, width W is more narrow in the central region M than at the ends. In another embodiment, width W is wider in the central region M than at the ends.

Figure 11A:
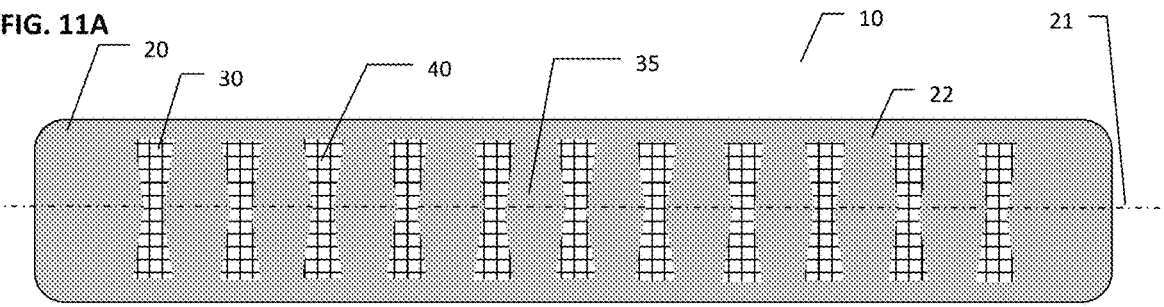
FIGS. 11A-B show embodiments of the skin closure device in schematic top views.

Referring now to FIG. 11A, an embodiment of Skin Closure System device 10 is shown, with openings 30 having concave rectangle or bow-tie shape having narrower width closer to axis 21 and wider width further from axis 21. Spacer areas 35 have elliptical or rhombus shape or similar, being wider closer to axis 21 and narrower further from axis 21.

Figure 11B:
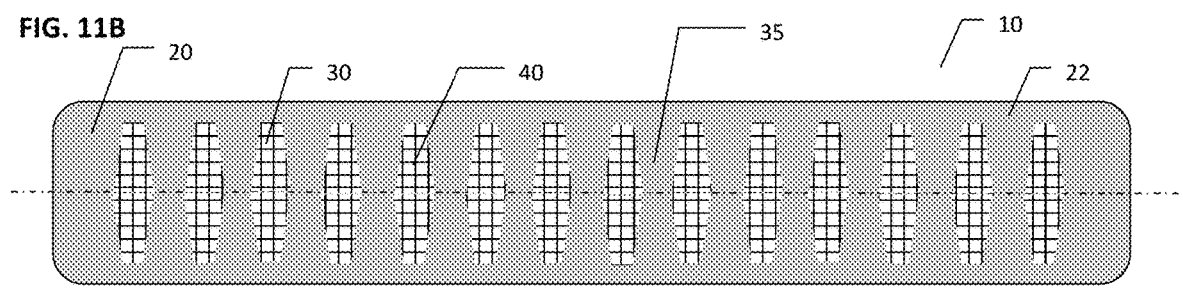

Referring now to FIG. 11B, an embodiment of Skin Closure System device 10 is shown, with openings 30 having elliptical or rhombus shape or similar, having wider width closer to axis 21 and narrower width further from axis 21. Spacer areas 35 have bow-tie shape or similar, being narrower closer to axis 21 and wider further from axis 21. Optimization of shape of openings 30 and/or spacer areas 35 results in more stretchability around the center or middle M of device 10.

Figure 12:
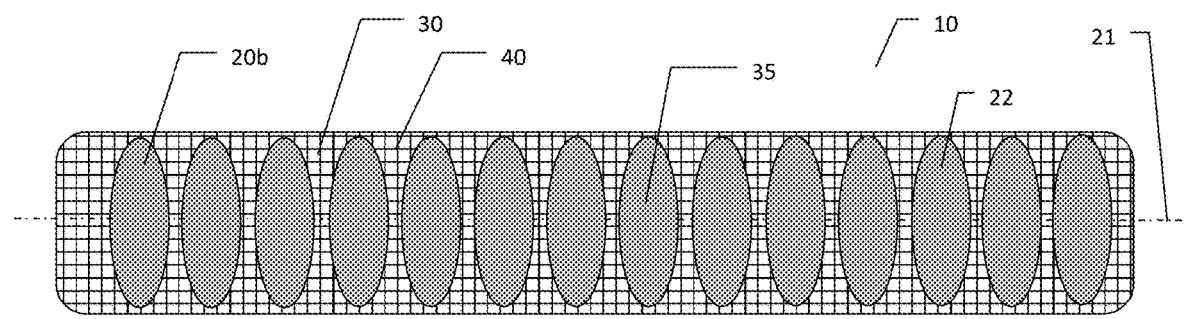
FIG. 12 shows an embodiment of the skin closure device in a schematic top view.

Referring now to FIG. 12, an embodiment of Skin Closure System device is shown, with tape 20 represented by elliptical non-connected islands 20*b* of little or no porosity. Islands 20*b* can be of varying width. Openings 30 are of bow-tie shape and are formed between islands 20*b* of mesh 40.

In one embodiment, there are narrow cuts (not shown) in spacer areas 35 separating openings 30, the cuts comprising narrow slits in tape 20 oriented perpendicular to axis 21 and having length not more than 80% of width W, such as 25, 50%. The cuts can be only between some openings 30 or between all openings 30.

Sizes

Tape 20 can be of any elongated shape to cover an articulating joint, such as elliptical, rectangular, and similar. Tape 20 can have ratio of length to width of about 1:2 to about 1:20, such as 1:5. The length of tape 20 is from about 10 cm to about 50 cm, such as 25 cm. The width of tape 20 is from 2 cm to 10 cm, such 3 cm, 5 cm.

Openings 30 can be rectangular, elliptical, circular, etc., and occupy from 30% to 80% of tape 20 area. Width W' of openings 30 is from 2 mm to 12 mm, more preferable 3 mm to 10 mm. The longitudinal dimension or length L' of the openings across the width of the tape W is configured so that openings occupy at least 60% of the tape width W, preferably 60 to 100%, more preferably 70-90% of W. Width W' of openings 30 is configured to be at least 5% of L', preferably 5%-100% of L', more preferably at 20-30% of L'.

Porosity of mesh 40 or tape 20 porated areas in openings 30 is defined by size of pores or holes being from about 0.01 mm$^2$ to about 4 mm$^2$, more preferably 0.1 mm$^2$ to 1 mm$^2$. Percent of open area in mesh 40, or ratio of area of holes to area of material surrounding holes within openings 30 is from about 95%-about 20%, more preferably 90%-40% constituting open area.

PSA

Optional pressure sensitive adhesive bands or stripes are disposed over lower surface 23, (such as shown in FIG. 2) covering from 10% to 90% of lower surface 23. Other shapes and forms of applying pressure sensitive adhesive are contemplated, including dots, squares, mixed angular bands, etc.

Initiator

In a preferred embodiment, initiators and/or accelerators or rate modifiers of adhesive polymerization or cross-linking can be releasably disposed on mesh 40 or releasably incorporated into mesh 40. For example, one or more chemical substances may be dispersed in or on mesh 40 such as being chemically bound, physically bound, coated, absorbed, or adsorbed to it.

For example, a polymerization initiator or accelerator or rate modifier may be loaded in or on mesh 40 so that the initiator or rate modifier provides the desired initiation or rate modification effect to a subsequently applied polymerizable adhesive composition. The polymerization initiator or rate modifier may be immobilized in or on mesh 40, so that the initiator or rate modifier does not become detached from mesh 40 and its residues are dispersed in the resultant polymeric material. Alternatively, for example, the polymerization initiator or rate modifier may be initially attached to mesh 40, but only in such a manner that it becomes mobilized or solubilized by a subsequently applied polymerizable adhesive composition and dispersed in the resultant polymeric material.

If desired, a combination of chemical substances may also be provided in or on mesh 40, to provide multiple effects. For example, a first chemical species (such as a polymerization initiator or rate modifier) may be immobilized in or on mesh 40, while a second, different chemical species (such as a bioactive material) may be detachably attached to mesh 40. Other combinations of chemical species and resultant effects are also envisioned.

When present in or on mesh 40, the chemical substances (i.e., polymerization initiator, rate modifier, and/or bioactive materials, or other additives), may be incorporated in or on mesh 40 in any suitable manner. For example, the chemical substance may be added to mesh 40 by contacting mesh 40 with a solution, mixture, or the like including the chemical substances. The chemical substance may be added to mesh 40, for example, by dipping, spraying, roll coating, gravure coating, brushing, vapor deposition, or the like. Alternatively, the chemical substance may be incorporated into or onto mesh 40 during manufacture of mesh 40, such as during molding.

The polymerization initiator or rate modifier loaded in or on mesh 40 may provide a number of advantages for example, so as to provide faster polymerization time. The concentration of polymerization initiator or rate modifier may be increased to provide even faster polymerization time.

Because the polymerization initiator or rate modifier is loaded directly in or on mesh 40, it is not necessary to mix the polymerizable adhesive composition with a polymerization initiator or rate modifier prior to application. This may allow a longer working time, where the polymerizable monomer composition may be more precisely and carefully applied over a longer period of time.

Such suitable initiators are known in the art and are described, for example, in U.S. Pat. Nos. 5,928,611 and 6,620,846, both incorporated herein by reference in their entireties, and U.S. Patent Application No. 2002/0037310, also incorporated herein by reference in its entirety. Quaternary ammonium chloride and bromide salts useful as polymerization initiators are particularly suitable. By way of example, quaternary ammonium salts such as domiphen bromide, butyrylcholine chloride, benzalkonium bromide, acetyl choline chloride, among others, may be used.

Benzalkonium or benzyltrialkyl ammonium halides such as benzyltrialkyl ammonium chloride may be used. When used, the benzalkonium halide may be benzalkonium halide in its unpurified state, which comprises a mixture of varying chain-length compounds, or it can be any suitable purified compound including those having a chain length of from about 12 to about 18 carbon atoms, including but not limited to C12, C13, C14, C15, C16, C17, and C18 compounds. By way of example, the initiator may be a quaternary ammonium chloride salt such as benzyltrialkyl ammonium chloride (BTAC).

Other initiators or accelerators may also be selected by one of ordinary skill in the art without undue experimentation. Such suitable initiators or accelerators may include, but are not limited to, detergent compositions; surfactants: e.g., nonionic surfactants such as polysorbate 20 (e.g., Tween 20™ from ICI Americas), polysorbate 80 (e.g., Tween 80™ from ICI Americas) and poloxamers, cationic surfactants such as tetrabutylammonium bromide, anionic surfactants such as sodium tetradecyl sulfate, and amphoteric or zwitterionic surfactants such as dodecyldimethyl(3-sulfopropyl) ammonium hydroxide, inner salt; amines, imines and amides, such as imidazole, arginine and povidine; phosphines, phosphites and phosphonium salts, such as triphenylphosphine and triethyl phosphite; alcohols such as ethylene glycol, methyl gallate; tannins; inorganic bases and salts, such as sodium bisulfate, calcium sulfate and sodium silicate; sulfur compounds such as thiourea and polysulfides; polymeric cyclic ethers such as monensin, nonactin, crown ethers, calixarenes and polymeric-epoxides; cyclic and acyclic carbonates, such as diethyl carbonate; phase transfer catalysts such as Aliquat 336; organometallics such as cobalt naphthenate and manganese acetylacetonate; and radical initiators or accelerators and radicals, such as di-t-butyl peroxide and azobisisobutyronitrile.

Mixtures of two or more, such as three, four, or more, initiators or accelerators may be used. A combination of multiple initiators or accelerators may be beneficial, for example, to tailor the initiator of the polymerizable monomer species. For example, where a blend of monomers is used, a blend of initiators may provide superior results to a single initiator. For example, the blend of initiators can provide one initiator that preferentially initiates one monomer, and a second initiator that preferentially initiates the other monomer, or can provide initiation rates to help ensure that both monomer species are initiated at equivalent, or desired non-equivalent, rates. In this manner, a blend of initiators can help minimize the amount of initiator necessary. Furthermore, a blend of initiators may enhance the polymerization reaction kinetics.

Adhesive

In one embodiment, liquid or semi-liquid adhesive 50 is polymerized or is cross-linking polymerized or is cross-linking after coming in contact with initiators and/or accelerators of adhesive polymerization and/or cross-linking.

Such initiators and/or accelerators can be coated or disposed non-releasably, i.e. immobilized in or on the mesh 40 while retaining activity to initiate or accelerate polymerization and/or cross-linking. In one embodiment, initiators and/or accelerators are disposed releasably, i.e. they can be at least partially released into and mix with flowing adhesive 50.

In a preferred embodiment, adhesive 50 is polymerized or is cross-linking after coming in contact with initiators and/or accelerators releasably disposed in or on the mesh 40. Rapid polymerization and/or crosslinking of adhesive 50 results in bonding of device 10 to tissue.

Adhesive 50 can be any type of biocompatible and rapidly cross-linkable and/or polymerizable compound or mixture of compounds. Rapidly cross-linkable and/or polymerizable means that after initiators or accelerators are added, or after the adhesive is formed from two or more components, it is capable of curing, i.e. cross-linking and/or polymerizing within 0.2 min to about 20 min, more preferably within 0.5 min to 10 min, such as 1, 2, 3, 5 min.

In one embodiment, adhesive 50 is formed prior to application onto mesh 40, for instance by mixing two components contained in separate barrels or a two-barrel syringe, by passing these two components through a mixing tip. In this embodiment, there is no crosslinking initiator or accelerator disposed inside of mesh 40. In one embodiment, adhesive 50 is formed by mixing fibrinogen and thrombin together.

In one embodiment, adhesive 50 comprises fibrinogen, and crosslinking initiator or accelerator disposed inside of mesh 40 comprises thrombin.

In a preferred embodiment, the polymerizable adhesive composition may comprise a polymerizable monomeric adhesive. In embodiments, the polymerizable adhesive composition comprises a polymerizable 1,1-disubstituted ethylene monomer formulation. In embodiments, the polymerizable adhesive composition comprises a cyanoacrylate formulation. In embodiments, synthetic polymerizable adhesive materials such as polyurethane, polyethylene glycol, acrylates, glutaraldehyde and biologically based adhesives may be used.

Suitable .alpha.-cyanoacrylate monomers which may be used, alone or in combination, include alkyl .alpha.-cyanoacrylates such as 2-octyl cyanoacrylate; dodecyl cyanoacrylate; 2-ethylhexyl cyanoacrylate; butyl cyanoacrylate such as n-butyl cyanoacrylate; ethyl cyanoacrylate; methyl cyanoacrylate or other .alpha.-cyanoacrylate monomers such as methoxyethyl cyanoacrylate; 2-ethoxyethyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate. In embodiments, the monomers are ethyl, n-butyl, or 2-octyl .alpha.-cyanoacrylate. Other cyanoacrylate monomers which may be used include alkyl ester cyanoacrylates, such as those prepared by the Knoevenagel reaction of an alkyl cyanoacetate, or an alkyl ester cyanoacetate, with paraformaldehyde, subsequent thermal cracking of the resultant oligomer and distillation.

Many other adhesive formulations can be used and are known to a skilled artisan. For example, mixtures containing PEG succinimidyl glutarate can be used as a flowable adhesive.

It should be understood that the foregoing disclosure and description of the embodiments of the present invention are illustrative and explanatory thereof and various changes in the size, shape and materials as well as in the description of the preferred embodiment may be made without departing from the spirit of the invention.

We claim:

1. A device for skin closure, comprising
    a) an elastic flat flexible tape elongated along a longitudinal axis and having a lower side and an opposing upper side,
    b) said tape comprising a mesh substrate;
    said tape having a pressure sensitive adhesive on at least a portion of the lower side, further comprising:
    (i) a removable mask releasably disposed on said tape and having substantially same shape as said tape;
    (ii) said mask having a plurality of openings arranged side-by-side with spaces between said openings oriented across the longitudinal axis such that the mesh substrate is exposed through the plurality of openings, wherein the openings occupy between 30% and 80% of a total area of the mask, and wherein each of the plurality of openings extends from a first area proximate to a first edge of the mask, across the longitudinal axis, and to a second area proximate to a second edge of the mask; and
    (iii) the mask further having one or more tabs configured for grasping for lift-off and removal of the mask.

2. The device of claim 1, wherein the mask is made of a polymeric flexible material.

3. The device of claim 2, wherein the polymeric flexible material is elastic.

4. The device of claim 2, wherein the polymeric flexible material is non-elastic.

5. The device of claim 1, wherein the mesh substrate is made of a polymeric flexible material that is elastic.

6. The device of claim 1, wherein the mesh substrate is impregnated with an initiator configured to react with a polymerizable adhesive to accelerate polymerization.

7. The device of claim 1, wherein the tape has a first thickness and the mesh substrate has a second thickness less than the first thickness.

8. The device of claim 1, wherein the mesh substrate is one of a porous nonwoven, a felt, a porous woven fabric, a textile, or a foam.

9. A device for skin closure, comprising:
    a) an flat flexible tape elongated along a central longitudinal axis and having a lower side and an opposing upper side,
    b) said tape having a pressure sensitive adhesive on at least a portion of the lower side,
    c) said tape having a plurality of openings arranged side-by-side with spaces between said openings oriented across the central longitudinal axis; and
    d) said openings further arranged above and below the central longitudinal axis of said tape and separated by axial spacer areas with no openings overlapping said central longitudinal axis, wherein the openings comprise a porous mesh and said axial spacer areas are non-porous, wherein the openings occupy between 30% and 80% of a total area of the tape,
    wherein a width of the openings is between 2 mm to 12 mm.

10. The device of claim 9, wherein the tape is made of a polymeric flexible material.

11. The device of claim 10, wherein the polymeric flexible material is elastic.

12. The device of claim 10, wherein the polymeric flexible material is non-elastic.

13. The device of claim 9, wherein the porous mesh is made of a polymeric flexible material that is elastic.

14. The device of claim 9, wherein the porous mesh includes an initiator configured to react with a polymerizable adhesive to accelerate polymerization.

15. The device of claim 9, wherein the porous mesh is one of a porous nonwoven, a felt, a porous woven fabric, a textile, or a foam.

\* \* \* \* \*